United States Patent
Pergolizzi et al.

(10) Patent No.: US 12,138,267 B2
(45) Date of Patent: Nov. 12, 2024

(54) METHODS OF TREATING RESPIRATORY DEPRESSION MODULATED BY A NON-OPIOID AGENT

(71) Applicant: Enalare Therapeutics Inc., Princeton, NJ (US)

(72) Inventors: Joseph Pergolizzi, Princeton, NJ (US); Thomas Miller, Princeton, NJ (US); Alfred Schweikert, Princeton, NJ (US)

(73) Assignee: Enalare Therapeutics Inc., Princeton, NJ (US)

( * ) Notice: Subject to any disclaimer, the term of this patent is extended or adjusted under 35 U.S.C. 154(b) by 68 days.

(21) Appl. No.: 17/979,192

(22) Filed: Nov. 2, 2022

(65) Prior Publication Data
US 2023/0140606 A1 May 4, 2023

Related U.S. Application Data

(60) Provisional application No. 63/274,722, filed on Nov. 2, 2021.

(51) Int. Cl.
*A61K 31/519* (2006.01)
*A61K 31/53* (2006.01)
*A61P 11/00* (2006.01)

(52) U.S. Cl.
CPC .......... *A61K 31/519* (2013.01); *A61K 31/53* (2013.01); *A61P 11/00* (2018.01)

(58) Field of Classification Search
None
See application file for complete search history.

(56) References Cited

U.S. PATENT DOCUMENTS

| | | | |
|---|---|---|---|
| 4,508,715 | A | 4/1985 | Booth et al. |
| 9,162,992 | B2 | 10/2015 | Mannion et al. |
| 9,351,972 | B2 | 5/2016 | Dax et al. |
| 2015/0291597 | A1 | 10/2015 | Mannion et al. |
| 2016/0256463 | A1 | 9/2016 | Pax et al. |
| 2017/0367987 | A1 | 12/2017 | Amson et al. |
| 2018/0141953 | A1 | 5/2018 | Dax et al. |
| 2018/0169006 | A1 | 6/2018 | Crystal et al. |
| 2018/0296565 | A1 | 10/2018 | Hsu |

FOREIGN PATENT DOCUMENTS

| | | |
|---|---|---|
| WO | 2017/015309 A1 | 1/2017 |
| WO | 2020/041006 A2 | 2/2020 |

OTHER PUBLICATIONS

Dahan, et al., "Averting Opioid-induced Respiratory Depression without Affecting Analgesia," Anesthesiology, Lippincott Williams & Wilking, Apr. 30, 2018, pp. 1027-1037, vol. 128, No. 5.
Cotten, Joseph F., M.D., Ph.D., "The Latest Pharmacologic Ventilator," The American Society of Anesthesiologists, Inc., Anesthesiology, 2014, pp. 442-444, VFol. 121, No. 3.
McLeod et al, "GAL-021, a new intravenous BKca-channel blocker, is well tolerated and stimulates ventilation in healthy volunteers," British Journal of Anaesthesia, 2014, pp. 875-883, vol. 113, No. 5, Oxford University Press.
Roozekrans, et al., "Two Studies on Reversal of Opiod-induced Respiratory Depression by BK-channel Blocker GAL021 in Human Volunteers," The American Society of Anesthesiologists, Inc., Lippincott Williams & Wilkins, Anesthesiology, 2014, pp. 459-468, vol. 121.
Roozekrans, et al., "Reversal of Opioid-Induced Respiratory Depression by BK-Channel Blocker GAL021: A Pharmacokinetic Modeling Study in Healthy Volunteers," Clinical Pharmacology & Therapeutics, Jun. 2015, pp. 641-649, vol. 97, No. 6.
Soni, et al., "Aminopyridine—A Review," Anaesth Intens Care, May 1982, pp. 120-126, vol. 10.
Van Der Schier, et al., "Opioid-induced respiratory depression: reversal by non-opioid drugs," F1000 Prime Reports, Sep. 4, 2014, 8 pgs.
Reents, et al., "Naloxone and Naltrexone. Application in COPD," Chest, American College of Chest Physicians, Jan. 1, 1998, pp. 217-219, vol. 92, No. 1.
International Search Report and Written Opinion of International Application No. PCT/US2022/048669 mailed Feb. 7, 2023, 11 pgs.

*Primary Examiner* — Zinna Northington Davis
(74) *Attorney, Agent, or Firm* — Lowenstein Sandler LLP

(57) ABSTRACT

Disclosed in certain embodiments is a method of treating respiratory depression modulated by a non-opioid agent comprising administering, to a patient in need thereof, an effective amount of a compound selected from Formula (I) as disclosed herein.

8 Claims, 10 Drawing Sheets

Abbreviations: SD = standard deviation; ENA low = ENA-001 low dose; ENA high = ENA-001 high dose; min = minutes.

Abbreviations: SD = standard deviation; ENA low = ENA-001 low dose; ENA high = ENA-001 high dose; min = minutes.

Abbreviations: SD = standard deviation; ENA low = ENA-001 low dose; ENA high = ENA-001 high dose; min = minutes.

Abbreviations: CO2 = carbon dioxide; SD = standard deviation; ENA low = ENA-001 low dose; ENA high = ENA-001 high dose; min = minutes.

Abbreviations: SD = standard deviation; ENA low = ENA-001 low dose; ENA high = ENA-001 high dose; min = minutes.

Abbreviations: SD = standard deviation; ENA low = ENA-001 low dose; ENA high = ENA-001 high dose; hrs = hours.

METHODS OF TREATING RESPIRATORY DEPRESSION MODULATED BY A NON-OPIOID AGENT

CROSS REFERENCE TO RELATED APPLICATION(S)

The present application claims priority to U.S. Provisional Patent Application No. 63/274,722, which was filed on Nov. 2, 2021, the entire contents of which are incorporated in its entirety.

FIELD OF THE DISCLOSURE

The present disclosure relates methods and compositions to treat respiratory depression modulated by a non-opioid agent.

BACKGROUND OF THE DISCLOSURE

The human body is critically dependent on the ventilatory control system for adequate uptake of oxygen and removal of carbon dioxide ($CO_2$). Opioid analgesics, through their actions on μ-opioid receptor expressed on respiratory neurons in the brainstem, may cause respiratory depression in certain situations such as overdose.

However, there are non-opioid agents that may cause respiratory depression in overdose or other situations. For example, anesthics such as propofol can cause respiratory depression that may be life threatening.

There exists a need in the art for methods of treatment and compounds to treat respiratory depression modulated by a non-opioid agent.

SUMMARY OF THE DISCLOSURE

In certain embodiments, the present disclosure is directed to methods of treatment and compounds to treat respiratory depression modulated by a non-opioid agent.

In certain embodiments, the present disclosure is directed to a method of treating respiratory depression modulated by a non-opioid agent comprising administering, to a patient in need thereof, an effective amount of a compound selected from Formula (I):

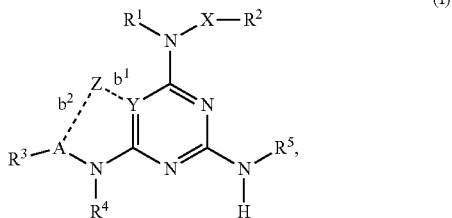

(I)

wherein:

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl, substituted alkynyl, cycloalkyl, substituted cycloalkyl, alkenyl, substituted alkenyl, —$NR^1R^2$, —$C(O)OR^1$, acyl, or aryl;

$R^4$ is H, alkyl, or substituted alkyl;

$R^5$ is H, alkyl, propargylic, substituted propargylic, homopropargylic, substituted homopropargylic, substituted alkyl, cycloalkyl, substituted cycloalkyl, alkenyl, substituted alkenyl, —$OR^1$, —$NR^1R^2$, —$C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and: (i) Z is H, bond $b^2$ is a single bond, and A is CH; or, (ii) Z is nil, bond $b^2$ is nil, and A is a single bond; and, if Y is C, then bond $b^1$ is a single bond, and: (i) Z is $CH_2$, bond $b^2$ is a single bond, and A is CH; or, (ii) Z is CH, bond $b^2$ is a double bond, and A is C;

or a salt thereof.

In certain embodiments, at least one substituent selected from the group consisting of $R^1$, $R^2$, $R^3$ and $R^5$, as described with respect to Formula (I) above, is alkynyl or substituted alkynyl.

In certain embodiments, the compound of Formula (I) is administered via a route that is selected from oral, intravenous, nasal, inhalational, topical, buccal, rectal, pleural, peritoneal, vaginal, intramuscular, subcutaneous, transdermal, epidural, intratrachael, otic, intraocular, or intrathecal route.

In certain embodiments, the present disclosure is directed to a pharmaceutical composition comprising an effective amount a compound selected from Formula (I) to treat respiratory depression modulated by a non-opioid agent:

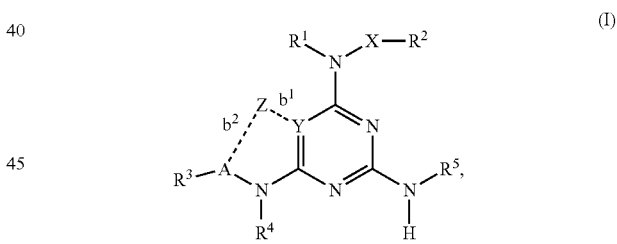

(I)

wherein:

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl, substituted alkynyl, cycloalkyl, substituted cycloalkyl, alkenyl, substituted alkenyl, —$NR^1R^2$, —$C(O)OR^1$, acyl, or aryl;

$R^4$ is H, alkyl, or substituted alkyl;

$R^5$ is H, alkyl, propargylic, substituted propargylic, homopropargylic, substituted homopropargylic, substituted alkyl, cycloalkyl, substituted cycloalkyl, alkenyl, substituted alkenyl, —OR$^1$, —NR$^1$R$^2$, —C(O)OR$^1$, acyl, aryl, substituted aryl, heteroaryl, substituted heteroaryl, heterocyclic, or substituted heterocyclic; or R$^3$ and R$^5$ combine as to form a biradical selected from the group consisting of 3,6,9-trioxa-undecane-1,11-diyl and 3,6-dioxa-octane-1,8-diyl;

R$^6$ is H, alkyl, substituted alkyl or alkenyl;

X is a bond, O or NR$^4$; and,

Y is N, CR$^6$ or C; wherein:

if Y is N or CR$^6$, then bond b$^1$ is nil and: (i) Z is H, bond b$^2$ is a single bond, and A is CH; or, (ii) Z is nil, bond b$^2$ is nil, and A is a single bond; and, if Y is C, then bond b$^1$ is a single bond, and: (i) Z is CH$_2$, bond b$^2$ is a single bond, and A is CH; or, (ii) Z is CH, bond b$^2$ is a double bond, and A is C;

or a salt thereof; and a pharmaceutically acceptable excipient.

In certain embodiments, the present disclosure is directed to a pharmaceutical composition comprising an effective amount a compound selected from Formula (I) to treat respiratory depression modulated by a non-opioid agent, as described above, where at least one substituent selected from the group consisting of R$^1$, R$^2$, R$^3$ and R$^5$ is alkynyl or substituted alkynyl.

In certain embodiments, the present disclosure is directed to a method of preparing any of the pharmaceutical compositions described herein.

DEFINITIONS

Figure 1:
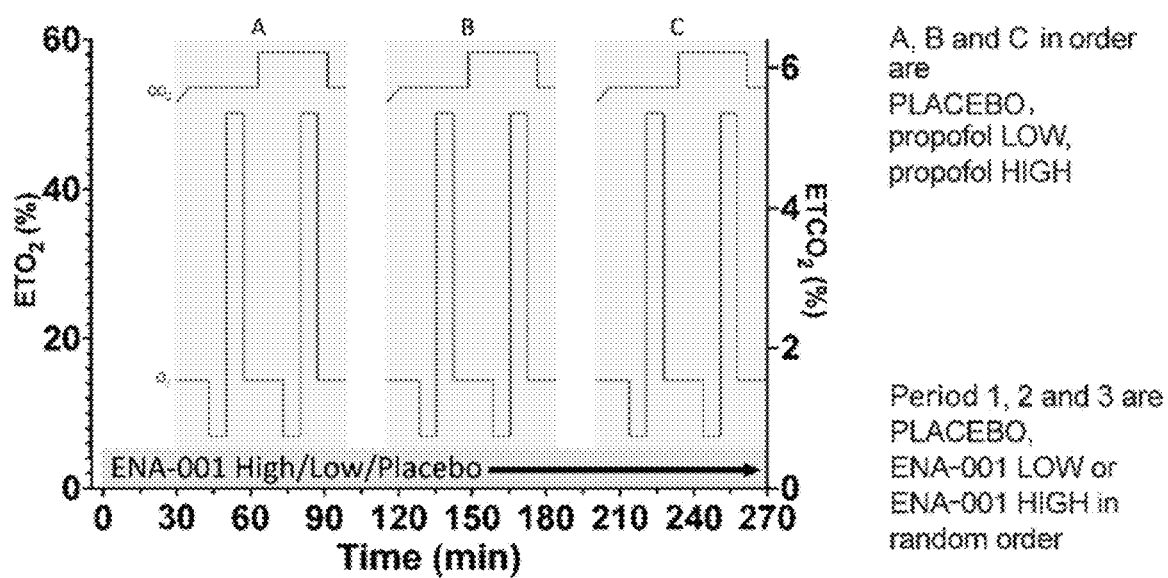
FIG. 1 is a schematic representation of the treatments and ventilatory conditions during each study period of the Example of the present disclosure.

As used herein, the singular forms "a," "an," and "the" include plural references unless the context clearly indicates otherwise. Thus, for example, reference to "an active agent" includes a single active agent as well as a mixture of two or more different active agent, and reference to an "excipient" includes a single excipient as well as a mixture of two or more different excipients, and the like.

As used herein, the term "about" in connection with a measured quantity, refers to the normal variations in that measured quantity, as expected by one of ordinary skill in the art in making the measurement and exercising a level of care commensurate with the objective of measurement and the precision of the measuring equipment. In certain embodiments, the term "about" includes the recited number ±10%, such that "about 10" would include from 9 to 11.

As used herein, the terms "active agent," "active ingredient," and "active pharmaceutical ingredient" refer to any material that is intended to produce a therapeutic, prophylactic, or other intended effect, whether or not approved by a government agency for that purpose. These terms with respect to specific agents include all pharmaceutically active agents, all pharmaceutically acceptable salts thereof, complexes, stereoisomers, crystalline forms, co-crystals, ether, esters, hydrates, solvates, and mixtures thereof, where the form is pharmaceutically active.

As used herein, the term "stereoisomers" is a general term for all isomers of individual molecules that differ only in the orientation of their atoms in space. It includes enantiomers and isomers of compounds with one or more chiral centers that are not mirror images of one another (diastereomers).

The term "enantiomer" or "enantiomeric" refers to a molecule that is nonsuperimposable on its mirror image and hence optically active wherein the enantiomer rotates the plane of polarized light in one direction by a certain degree, and its mirror image rotates the plane of polarized light by the same degree but in the opposite direction.

The term "chiral center" refers to a carbon atom to which four different groups are attached.

The term "patient" refers to a subject, an animal or a human, who has presented a clinical manifestation of a particular symptom or symptoms suggesting the need for treatment, who is treated preventatively or prophylactically for a condition, or who has been diagnosed with a condition to be treated. The term "subject" is inclusive of the definition of the term "patient" and does not exclude individuals who are otherwise healthy.

"Pharmaceutically acceptable salts" or "salts" include, but are not limited to, inorganic acid salts such as hydrochloride, hydrobromide, hydroiodic, sulfate, hydrogen sulfate, phosphate, nitric, carbonic, sulfuric, phosphoric (including hydrogen phosphate and dihydrogen phosphate), and the like; organic acid salts such as an oxalate, a malonate, a citrate, a fumarate, a lactate, a malate, a succinate, formate, acetate, trifluoroacetate, maleate, tartrate, a gluconate, a benzoate, a salicylate, a xinafoate, a pamoate, an ascorbate, an adipate, a cinnamte, and the like; sulfonates such as methanesulfonate, benzenesulfonate, p-toluenesulfonate and the like; amino acid salts such as arginate, asparaginate, glutamate and the like; metal salts such as zinc salt, sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, discyclohexylamine salt, N,N'-dibenzylethylenediamine salt, chloroprocaine, choline, diethanolamine, ethylenediamine, meglumine (N-methylglucamine) and procaine, and the like. These salts may be present in the form of a hydrate, a solvate, or a crystalline polymorph. In certain embodiments, appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. All of these salts may be prepared by conventional means from the corresponding compound of the invention by reacting, for example, the appropriate acid or base with the compound of the invention. *Handbook of Pharmaceutical Salts: Properties, and Use* (P. H. Stahl & C. G. Wermuth eds., Verlag Helvetica Chimica Acta, 2002) [1].

The term "disease" or "diseases" or "condition" or "conditions" refers to those medical conditions that can be treated or prevented by administration to a subject of an effective amount of an active agent.

The terms "treatment of" and "treating" includes the lessening of the severity of or cessation of a condition or lessening the severity of or cessation of symptoms of a condition. In certain embodiments, the terms "treatment" or "treating" with respect to a condition means administration with the intent to provide a pharmacodynamics effect, regardless of the outcome. In certain embodiments, "treatment" or "treating" means "having positive effect on a condition" and encompass reduction in the severity, amelioration, and/or alleviation of at least one symptom of a condition; a reduction, amelioration, and/or alleviation in the severity of the conditions; delay, prevention, or inhibition of the progression of the condition; or a perceived improvement or benefit as a result of the treatment. Treatment, as used herein, does not require total curing of the condition. In certain embodiments, a composition of the present disclosure may provide improvement to a patient's quality of life, or delay, prevent, inhibit the onset of one or more symptoms of a condition, or provide a perceived benefit.

The terms "prevention of" and "preventing" includes the avoidance of the onset of a condition.

The term "therapeutically effective amount" is intended to include an amount of an active agent, or an amount of the combination of active agents, e.g., to treat or prevent the condition, or to treat the symptoms of the condition, in a subject.

The term "effective amount" is intended to include an amount of a component, or an amount of a combination of component, to achieve a certain result or property, for instance, an effective amount of a pH adjusting agent to achieve a pH of 6.0 is intended to include an amount of one or more pH adjusting agents to arrive at a pH of 6.0.

The terms "application," "apply," and "applying" with respect to a disclosed topical composition, or method of using a disclosed topical composition, refer to any manner of administering a topical composition to the skin of a patient which, in medical or cosmetology practice, delivers the composition to the patient's skin surface. Smearing, rubbing, spreading, spraying a disclosed topical composition, with or without the aid of suitable devices, on a patient's skin are all included within the scope of the term "application," as used herein. The terms "topical" or "topically" with respect to administration or application of a disclosed formulation refer to epicutaneous administration or application, or administration onto skin.

As used herein, "oral delivery" or "oral administration" refers to a route of administration wherein the composition is taken through the mouth. Oral administration is a part of enteral administration, which also includes buccal (dissolved inside the cheek), sublabial (dissolved under the lip), and sublingual administration (dissolved under the tongue). In certain embodiments, oral administration includes a route of administration wherein the composition is ingested. In certain embodiments, oral administration includes a route of administration wherein the composition is inhaled.

As used herein, "parenteral administration" refers to a route of administration wherein the pharmaceutical dosage form is injected, e.g., to the muscle (intramuscular administration), to the vein (intravenous administration), under the skin (subcutaneous administration).

The phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

As used herein, the term "alkyl," by itself or as part of another substituent means, unless otherwise stated, a straight or branched chain hydrocarbon having the number of carbon atoms designated (i.e. C1-C10 means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is (C1-C6) alkyl, such as, but not limited to, ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e. C3-C6 means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is (C3-C6)cycloalkyl, such as, but not limited to, cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —CH2-CH=CH2.

As used herein, the term "alkynyl," employed alone or in combination with other terms, means, unless otherwise stated, a stable straight chain or branched chain hydrocarbon group with a triple carbon-carbon bond, having the stated number of carbon atoms. Examples include ethynyl and propynyl, and the higher homologs and isomers.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, tetrahydro-2-H-pyranyl, —NH2, —N(CH3)2, (1-methyl-imidazol-2-yl), pyridin-2-yl, pyridin-3-yl, pyridin-4-yl, —C(=O) OH, trifluoromethyl, —C≡N, —C(=O)O(C1-C4)alkyl, —C(=O)NH2, —C(=O)NH(C1-C4)alkyl, —C(=O)N ((C1-C4)alkyl)2, —SO2NH2, —C(=NH)NH2, and —NO2, preferably containing one or two substituents selected from halogen, —OH, alkoxy, —NH2, trifluoromethyl, —N(CH3)2, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are (C1-C3) alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl or —$CH_2$-phenyl (benzyl). Preferred is aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Preferred is substituted aryl ($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$— pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

In yet another embodiment, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, with straight being preferred.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

DETAILED DESCRIPTION

Certain embodiments of the instant disclosure are directed to methods of treating respiratory depression modulated by a non-opioid agent including administering to a patient in need thereof, an effective amount of a compound selected from Formula (I) described herein. The method of the present disclosure was found in certain embodiments to demonstrate efficacy against overdose of a non-opioid central depressant, such as propofol. In certain embodiments, the method of the present disclosure enhances the body's ability to react to adverse changes in blood gases. For example, the acuity (sensitivity) of the internal feedback loop. In certain embodiments, the method of the present disclosure is capable of imparting sensitivity back into a regulatory control mechanism that is blunted at the central control point by upregulating a peripheral control point. This is different from opioid antagonists such as naloxone which reverse respiratory depression by competitively displacing opioids from the opioid receptors. That is, antagonists reverse all sequalae of opioids, including beneficial therapeutic effects.

In certain embodiments of the instant disclosure, the method described herein restores the ability of the respiratory system to work despite the central blunting. It has also been found in certain embodiments that the dosing of the compound enhances sensitivity during exposure to anesthetic agents, but does not overtly drive hyperventilation as the patient starts to emerge. In certain embodiments, a higher dose may acutely drive breathing, whereas lower doses may modulate breathing.

Certain embodiments of the instant disclosure are directed to methods of treating respiratory depression modulated by a non-opioid agent comprising administering, to a patient in need thereof, an effective amount of a compound selected from Formula (I):

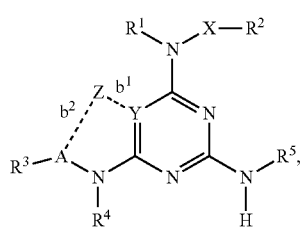

wherein:

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl, substituted alkynyl, cycloalkyl, substituted cycloalkyl, alkenyl, substituted alkenyl, —$NR^1R^2$, —$C(O)OR^1$, acyl, or aryl;

$R^4$ is H, alkyl, or substituted alkyl;

$R^5$ is H, alkyl, propargylic, substituted propargylic, homopropargylic, substituted homopropargylic, substituted alkyl, cycloalkyl, substituted cycloalkyl, alkenyl, substituted alkenyl, —$OR^1$, —$NR^1R^2$, —$C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and: (i) Z is H, bond $b^2$ is a single bond, and A is CH; or, (ii) Z is nil, bond $b^2$ is nil, and A is a single bond; and, if Y is C, then bond $b^1$ is a single bond, and: (i) Z is $CH_2$, bond $b^2$ is a single bond, and A is CH; or, (ii) Z is CH, bond $b^2$ is a double bond, and A is C;

or a salt thereof.

Certain embodiments of the instant disclosure are directed to methods of treating respiratory depression modulated by a non-opioid agent comprising administering, to a patient in need thereof, an effective amount of a compound selected from Formula (I):

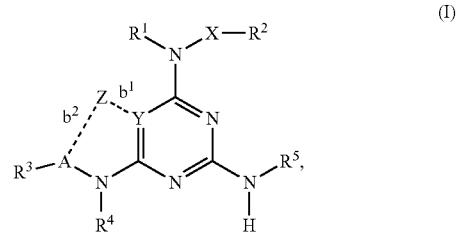

wherein:

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl, substituted alkynyl, cycloalkyl, substituted cycloalkyl, alkenyl, substituted alkenyl, —$NR^1R^2$, —$C(O)OR^1$, acyl, or aryl;

$R^4$ is H, alkyl, or substituted alkyl;

$R^5$ is H, alkyl, propargylic, substituted propargylic, homopropargylic, substituted homopropargylic, substituted alkyl, cycloalkyl, substituted cycloalkyl, alkenyl, substituted alkenyl, —$OR^1$, —$NR^1R^2$, —$C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl; wherein at least one substituent selected from the group consisting of $R^1$, $R^2$, $R^3$ and $R^5$ is alkynyl or substituted alkynyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and: (i) Z is H, bond $b^2$ is a single bond, and A is CH; or, (ii) Z is nil, bond $b^2$ is nil, and A is a single bond; and, if Y is C, then bond $b^1$ is a single bond, and: (i) Z is $CH_2$, bond $b^2$ is a single bond, and A is CH; or, (ii) Z is CH, bond $b^2$ is a double bond, and A is C;

or a salt thereof.

Certain embodiments of the instant disclosure are directed to methods of treating respiratory depression modulated by a non-opioid agent comprising administering, to a patient in need thereof, an effective amount of a compound selected from Formula (I):

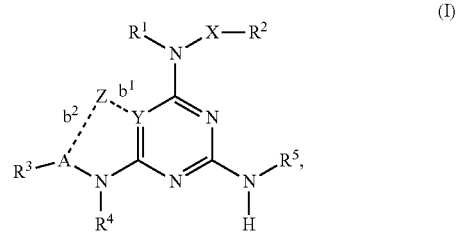

wherein:

$R^1$ and $R^2$ are independently H, alkyl, substituted alkyl, cycloalkyl, substituted cycloalkyl, alkenyl, substituted alkenyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, cycloalkyl, substituted cycloalkyl, alkenyl, substituted alkenyl, —$NR^1R^2$, —$C(O)OR^1$, acyl, or aryl;

$R^4$ is H, alkyl, or substituted alkyl;

$R^5$ is H, alkyl, substituted alkyl, cycloalkyl, substituted cycloalkyl, alkenyl, substituted alkenyl, —$OR^1$, —$NR^1R^2$, —$C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and: (i) Z is H, bond $b^2$ is a single bond, and A is CH; or, (ii) Z is nil, bond $b^2$ is nil, and A is a single bond; and, if Y is C, then bond $b^1$ is a single bond, and: (i) Z is $CH_2$, bond $b^2$ is a single bond, and A is CH; or, (ii) Z is CH, bond $b^2$ is a double bond, and A is C;

or a salt thereof.

In one embodiment, $R^3$ is H, alkyl, substituted alkyl, cycloalkyl, substituted cycloalkyl, alkenyl, or substituted alkenyl. In another embodiment, $R^5$ is H, alkyl, substituted alkyl, cycloalkyl, substituted cycloalkyl, alkenyl, substituted alkenyl, or acyl.

Certain embodiments of the instant disclosure are directed to methods of treating respiratory depression modulated by a non-opioid agent comprising administering, to a patient in need thereof, an effective amount of a compound selected from Formula (I):

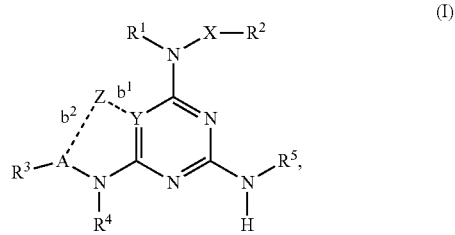

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl or substituted alkynyl;

$R^4$ is H, alkyl, or substituted alkyl;

$R^5$ is alkyl, propargylic, substituted propargylic, homopropargylic, or substituted homopropargylic, wherein at least one substituent selected from the group consisting of $R^1$, $R^2$, $R^3$ and $R^5$ is alkynyl or substituted alkynyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and:

(i) Z is H, bond $b^2$ is a single bond, and A is CH; or, (ii) Z is nil, bond $b^2$ is nil, and A is a single bond; and, if Y is C, then bond $b^1$ is a single bond, and:

(i) Z is $CH_2$, bond $b^2$ is a single bond, and A is CH; or, (ii) Z is CH, bond $b^2$ is a double bond, and A is C;

or a salt thereof.

In certain embodiments, (i) $R^3$ is H, alkyl or substituted alkyl, and $R^5$ is propargylic, substituted propargylic, homopropargylic, or substituted homopropargylic, or (ii) $R^3$ is H or alkynyl, and $R^5$ is alkyl, propargylic, substituted propargylic, homopropargylic, or substituted homopropargylic.

In one embodiment, the at least one compound of formula (I) is selected from the group consisting of: (i) Y is N, bond b1 is nil, Z is H, bond b2 is a single bond, A is CH, and the at least one compound is a compound of formula (II-a) or a salt thereof:

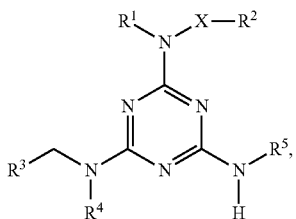

(II-a)

and (ii) Y is N, bond b1 is nil, Z is nil, bond b2 is nil, and A is a bond, and the compound of the invention is a compound of formula (II-b) or a salt thereof:

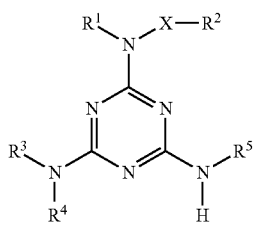

(II-b)

In one embodiment, the at least one compound of formula (I) is selected from the group consisting of: (i) Y is $CR^6$, bond $b^1$ is nil, Z is H, bond $b^2$ is a single bond, A is CH, and the at least one compound is a compound of formula (III-a) or a salt thereof:

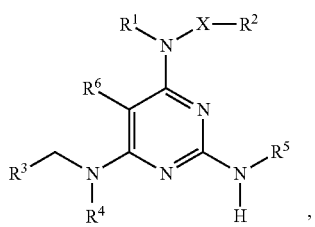

(III-a)

and (ii) Y is $CR^6$, bond $b^1$ is nil, Z is nil, bond $b^2$ is nil, and A is a bond, and the compound of the invention is a pyrimidine of formula (III-b) or a salt thereof:

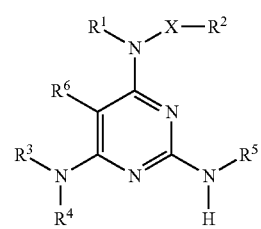

(III-b)

In one embodiment, Y is C, bond $b^1$ is a single bond, Z is $CH_2$, bond $b^2$ is a single bond, A is CH, and said at least one compound is a compound of formula (IV) or a salt thereof:

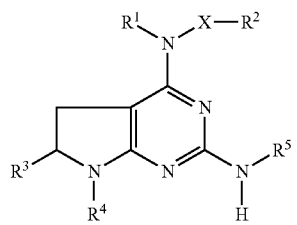

(IV)

In one embodiment, Y is C, bond $b^1$ is a single bond, Z is CH, bond $b^2$ is a double bond, A is C, and said at least one compound is a compound of formula (V) or a salt thereof:

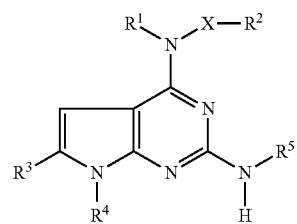

(V)

In one embodiment, the at least one compound is selected from the group consisting of: N-(4,6-Bis-methylamino-[1,3,5]triazin-2-yl)-N,O-dimethyl-hydroxylamine (XX), N-(4,6-Bis-ethylamino-[1,3,5]triazin-2-yl)-N,O-dimethyl-hydroxylamine (XXII), N-(4-Cyclopropylmethylamino)-N-(6-n-propylamino) [1,3,5]triazin-2-yl)-N,O-dimethyl-hydroxylamine (XXV), N-(4-Ethylamino)-N-(6-n-propylamino)-[1,3,5]triazin-2-yl)-N,O-dimethyl-hydroxylamine (XXVII), N-(Bis-4,6-(2-methylpropylamino)) [1,3,5]triazin-2-yl)-N,O-dimethyl-hydroxylamine (XXIX), N-(Bis-4,6-(2,2-dimethylpropylamino)) [1,3,5]triazin-2-yl)-O,N-dimethyl-hydroxylamine (XXXI), 4,6-Bis-N-cyclopropylamino-[1,3,5]triazin-2-yl)-N,O-dimethyl-hydroxylamine hydrochloride (XXXIII), N-(4,6-Bis-n-propylamino-[1,3,5]triazin-2-yl)-O,N-dimethyl-hydroxylamine (XXXV), N-(4-(Methoxy(methyl)amino)-6-(propylamino)-1,3,5-triazin-2-yl)propionamide (XL), N-(4,6-Bis-propylamino-[1,3,5]triazin-2-yl)-O-methyl-hydroxylamine (XLI), O-Allyl-N-(4,6-bis-propylamino-[1,3,5]triazin-2-yl)-hydroxylamine (XLIII), N-(4,6-Bis-propylamino-[1,3,5]triazin-2-yl)-hydroxylamine (XLV), 6-(Methoxy(methyl)amino)-N2-propyl-1,3,5-triazine-2,4-diamine (XLVII), N-(4,6-Bis-propylamino-[1,3,5]triazin-2-yl)-N-methyl-hydroxylamine (XLVIII), O-Benzyl-N-(4,6-bis-propylamino-[1,3,5]triazin-2-yl)-N-methyl-hydroxylamine (LIII), N-(4,6-Bis-propylamino-[1,3,5]triazin-2-yl)-N-isopropyl-hydroxylamine (LV), 6-[1,2]Oxazinan-2-yl-N,N'-dipropyl-[1,3,5]triazine-2,4-diamine (LVII), N-(4,6-Bis-propylamino-[1,3,5]triazin-2-yl)-O-isopropyl-N-methyl-hydroxylamine (LXIV), O-Benzyl-N-(4,6-bis-propylamino-[1,3,5]triazin-2-yl)-N-ethyl-hydroxylamine (LXVIII), N-(4,6-Bis-propylamino-[1,3,5]triazin-2-yl)-O-isopropyl-hydroxylamine (LXX), 6-((Benzyloxy)(isopropyl)amino)-N2,N4-dipropyl-1,3,5-triazine-2,4-diamine (LXXII), N-(4,6-Bis-propylamino-[1,3,5]triazin-2-yl)-N-ethyl-0-isopropyl-hydroxylamine (LXXVI), N-(4,6-Bis-propylamino-[1,3,5]triazin-2-yl)-O-isobutyl-N-methyl-hydroxylamine (LXXXII), 6-(Methyl(thiophen-2-ylmethoxy)amino)-N2,N4-dipropyl-1,3,5-triazine-2,4-diamine (LXXXIV), N-(4,6-Bis-propylamino-[1,3,5]triazin- 2-yl)-O-cyclopropylmethyl-N-methyl-hydroxylamine (XCI), N-(4,6-Bis-propylamino-[1,3,5]triazin-2-yl)-O-ethyl-N-methyl-hydroxylamine (XCVI), N-(4,6-Bis-propylamino-[1,3,5]triazin-2-yl)-O-(2,2-difluoro-ethyl)-hydroxylamine (C), 4-N-(2-Dimethylaminoethyl)amino-6-N-(n-propyl)amino-[1,3,5]triazin-2-yl)-N,O-dimethyl-hydroxylamine (CIII), 4-N-(3-(1-N-Methylimidazol-2-yl)-propyl)-amino-6-N-(n-propyl)amino-[1,3,5]triazin-2-yl)-N,O-dimethyl-hydroxylamine (CV), 4-N-(1-N-Methylimidazol-2-yl)-methylamino-6-N-(n-propyl)amino-[1,3,5]triazin-2-yl)-O,N-dimethyl-hydroxylamine (CVII), 4,6-Bis-(N-(2-dimethylaminoethyl)amino)-[1,3,5]triazin-2-yl)-N,O-dimethyl-hydroxylamine (CIX), 4,6-Bis-(N-(pyridin-4-ylmethyl)amino)-[1,3,5]triazin-2-yl)-N,O-dimethyl-hydroxylamine (CXI), 4,6-Bis-[N-(3-methoxy-n-propyl)amino]-[1,3,5]triazin-2-yl)-N,O-dimethyl-hydroxylamine (CXIII), 4,6-Bis-[N-(tetrahydropyran-4-ylmethyl)amino]-[1,3,5]triazin-2-yl)-N,O-dimethyl-hydroxylamine (CXV), N-(5,8,11-Trioxa-2,14,16,18,19-pentaazabicyclo[13.3.1]-nonadeca-1(18),15(19),16(17)-trien-17-yl)-N,O-dimethyl-hydroxylamine (CXVII), N-(4,6-Bis-propylamino-[1,3,5]triazin-2-yl)-N',N'-dimethylhydrazine (XLVI), N-(4,6-Bis-propylamino-[1,3,5]triazin-2-yl)-N-methyl-N'-methylhydrazine (XLIX), a salt thereof and mixtures thereof. In another embodiment, the salt is hydrogen sulfate or hydrochloride.

In one embodiment, the at least one compound is 2,6-bis-(N-n-propylamino)-[1,3]pyrimidin-4-yl)-N,O-dimethyl-hydroxylamine N-(4-(Methoxy(methyl)amino)-6-(propylamino)-1,3,5-triazin-2-yl)propionamide or a salt thereof. In another embodiment, the salt is hydrogen sulfate or hydrochloride.

In one embodiment, the at least one compound is N-(4-(Methoxy(methyl)amino)-6-(propylamino)-1,3,5-triazin-2-yl)propionamide or a salt thereof. In another embodiment, the salt is hydrogen sulfate or hydrochloride.

In one embodiment, the at least one compound is selected from the group consisting of: 2-(n-Propyl)amino-4-(i-propylamino-7-methyl-pyrrolidino[2,3-d]pyrimidine (CXXVI), 2-(n-Propyl)amino-4-dimethylamino-7-methyl-pyrrolidino[2,3-d]pyrimidine (CXXVIII), 2-(n-Propyl)amino-4-methylamino-7-methyl-pyrrolidino[2,3-d]pyrimidine (CXXXI), 2-(n-Propyl)amino-4-(i-propyl)amino-7-i-propyl-pyrrolidino[2,3-d]pyrimidine (CXXXVI), 2,4-Bis-(n-propyl)amino-7H-pyrrolidino[2,3-d]pyrimidine (CXLIX), 2-(n-Propyl)amino-4-(4-hydroxypiperidin-1-yl)-7-methyl-pyrrolidino[2,3-d]pyrimidine (CLII), 8-(7-Methyl-2-(propylamino)-pyrrolidino[²,3-d]pyrimidin-4-yl)-8-azabicyclo[3.2.1]octan-3-ol (CLV), a salt thereof and mixtures thereof. In another embodiment, the salt is hydrogen sulfate or hydrochloride.

In one embodiment, the at least one compound is selected from the group consisting of: N-(2-Propylamino-7H-pyrrolo[2,3d]pyrimidin-4-yl)-O,N-dimethyl-hydroxylamine (CXLI), N-(2-(Propen-2-yl)amino-7-methyl-pyrrolo[2,3d]pyrimidin-4-yl)-N,O-dimethyl-hydroxylamine (CLVIII), N-(2-(Propen-2-yl)amino-7-methyl-pyrrolo[2,3d]pyrimidin-4-yl)-O-methyl-hydroxylamine (CLX), N-(2-n-Propylamino-7-methyl-pyrrolo[2,3d]pyrimidin-4-yl)-O,N-dimethyl-hydroxylamine (CLXII), N-(2-n-Propylamino-7-methyl-pyrrolo[2,3d]pyrimidin-4-yl)-O-methyl-hydroxylamine (CLXIV), N-(2-n-Propylamino-7-methyl-pyrrolo[2,3d]pyrimidin-4-yl)-methyl-hydroxylamine (CLXVI), N-Methyl-N-(2-n-propylamino-7-methyl-pyrrolo[2,3d]pyrimidin-4-yl)-hydrazine (CLXVIII), N,N-dimethyl-N'-(2-n-propylamino-7-methyl-pyrrolo[2,3d]pyrimidin-4-yl)-hydrazine (CLXX), a salt thereof and mixtures thereof. In another embodiment, the salt is hydrogen sulfate or hydrochloride.

In certain embodiments, the compound is selected from the group consisting of O,N-dimethyl-N-[4-(n-propylamino)-6-(prop-2-ynylamino-[1,3,5]triazin-2-yl]-hydroxylamine; N-methyl-N'-n-propyl-N''-prop-2-ynyl-[1,3,5]triazine-2,4,6-triamine; a salt thereof; and any combinations thereof.

In certain embodiments the Compound A below is utilized in the present invention is

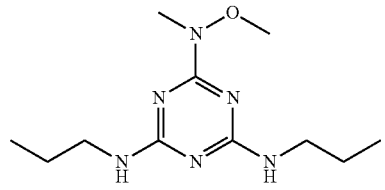 [SMILES: CCCNc1nc(NCCC)nc(N(C)OC)n1]

or a pharmaceutically acceptable salt thereof.

In certain embodiments, the compound of Formula (I) is selected from compounds described in U.S. Pat. No. 9,162,992 and/or in U.S. Pat. No. 9,351,972 and/or in United States Patent Application Publication No. 2015-0291597, now abandoned, the teachings of which are incorporated by reference herein in their entirety.

In certain embodiments, the non-opioid agent is a central nervous system depressant.

In certain embodiments, the central nervous system depressant is a surgical anesthetic.

In certain embodiments, the surgical anesthetic is propofol, fospropofol, ketamine, thiopental, methohexital, etomidate, sevoflurane, isoflurane, desflurane or a pharmaceutically acceptable salt thereof.

In certain embodiments, the patient exhibits a restored ventilatory sufficiency.

In certain embodiments, the patient exhibits restored ventilator sufficiency under normal sedation, under low sedation or under high sedation.

In certain embodiments, the patient exhibits restored ventilator sufficiency under overdose.

In certain embodiments, the patient shows increased ventilatory responsiveness.

In certain embodiments, the patient shows increased ventilatory responsiveness to hypoxemic events.

In certain embodiments, the patient shows increased ventilatory responsiveness to hypercapnic events.

In certain embodiments, ventilatory degradation in the patient is avoided or minimized.

In certain embodiments, ventilatory degradation in the patient is avoided or minimized during periods of hypercapnia.

In certain embodiments, the administration route is selected from oral, intravenous, nasal, inhalational, topical, buccal, rectal, pleural, peritoneal, vaginal, intramuscular, subcutaneous, transdermal, epidural, intratracheal, otic, intraocular, or intrathecal route.

The method of any preceding claim wherein the therapeutic effect of the non-opioid agent is maintained.

In certain embodiments, the therapeutic effect is not decreased.

In certain embodiments, the anesthetic effect is maintained.

In certain embodiments, the anesthetic effect is not decreased.

In certain embodiments, the patient exhibits an improvement in hypoxia.

In certain embodiments, the patient exhibits an improvement in hypercapnia.

In certain embodiments, the improvement is at least 5%, at least 10% at least 15%, at least 20% or at least 25%.

In certain embodiments, the patient exhibits an improvement in minute ventilation.

In certain embodiments, the improvement is at least 5%, at least 10% at least 15%, at least 20% or at least 25% as measured by Hypoxic Ventilatory Sensitivity (ΔVentilation/ΔSaturation=Hypoxic Sensitivity in L/min per % desaturation).

In certain embodiments, the patient has a positive ventilator response under normocapnic and mild hypercapnic conditions during normoxia.

In certain embodiments, the patient maintains ventilator response under normocapnic and mild hypercapnic conditions during normoxia.

In certain embodiments, the patient does not exhibit a side effect or experience a clinically significant side effect as measured by one or more of reported adverse events, physical examinations, vital signs, 12-lead ECGs, clinical laboratory test results and Columbia-Suicide Severity Rating Scale (C-SSRS) responses.

In certain embodiments, the patient does not exhibit clinically significant change in cardiovascular response.

In certain embodiments, the patient exhibits a therapeutic effect as measured by Hypoxic sensitivity (ΔVentilation/ΔSaturation).

In certain embodiments, the patient exhibits a therapeutic effect as measured by tidal volume (VT).

In certain embodiments, the patient exhibits a therapeutic effect as measured by respiratory rate (breaths/min).

In certain embodiments, the patient exhibits a therapeutic effect as measured by minute ventilation (VE).

In certain embodiments, the patient exhibits a therapeutic effect as measured by transcutaneous $CO_2$ measurement and/or end-tidal $CO_2$ (mmHg).

In certain embodiments, the patient exhibits a therapeutic effect as measured by transcutaneous hemoglobin saturation ($SpO_2$ in %).

In certain embodiments, the patient exhibits a therapeutic effect as measured by arterial blood gases.

In certain embodiments, the therapeutic effect is measured by BIS.

In certain embodiments, the patient exhibits a therapeutic effect as measured by hemodynamic parameters from arterial line monitoring.

In certain embodiments, the change is at least 5%, at least 10% at least 15%, at least 20% or at least 25%.

In certain embodiments, the administration is intravenously.

In certain embodiments, the compound of formula (I) is administered at a rate of from about 0.10 mg/kg/hour to about 10 mg/kg/hour.

In certain embodiments, the compound of formula (I) is administered at a rate of from about 0.50 mg/kg/hour to about 5 mg/kg/hour.

In certain embodiments, the compound of formula (I) is administered at a rate of from about 0.40 mg/kg/hour to about 1.0 mg/kg/hour.

In certain embodiments, the compound of formula (I) is administered at a rate of about 0.40 mg/kg/hour.

In certain embodiments, the compound of formula (I) is administered at a rate of about 1.0 mg/kg/hour.

In certain embodiments, the invention further comprises administering a loading dose.

In certain embodiments, the loading dose is from about 0.50 mg/kg/hour to about 5 mg/kg/hour.

In certain embodiments, the loading dose is from about 1.0 mg/kg/hour to about 3.0 mg/kg/hour.

In certain embodiments, the loading dose is about 2.0 mg/kg/hour.

In certain embodiments, the total time of administration is from about 5 minutes to about 24 hours.

In certain embodiments, the total time is from about 30 minutes to about 6 hours or from about 1 hour to about 3 hours.

In certain embodiments, the loading dose is administered as a bolus.

In certain embodiments, the loading dose is administered for a time of less than 1 hour, less than 45 minutes, less than 30 minutes, less than 25 minutes, less than about 10 minutes, about 10 minutes or about 20 minutes.

In certain embodiments, administration may be selected from oral, intravenous (e.g., continuous infusion or bolus injection), nasal, inhalational, topical, buccal, rectal, pleural, peritoneal, vaginal, intramuscular, subcutaneous, transdermal, epidural, intratrachael (e.g., intratracheal instillation or intratracheal inhalation), otic, intraocular, or intrathecal route. Non-limiting exemplary suitable pulmonary administration may be with a metered dose inhaler, nebulizer, soft mist inhaler, a high efficiency nebulizer, ultrasonic nebulizer, dry powder inhaler, a continuous positive airway pressure (CPAP) machine, a bilevel positive airway pressure machine (BiPAP), or a ventilator.

In certain embodiments, the terminal half-life is about 1 to about 15 hours, about 2 to about 14 hours, about 3 to about 13 hours, about 4 to about 12 hours, about 4 to about 11 hours, about 5 to about 10 hours, about 6 to about 9 hours, or about 7 to about 8 hours.

In certain embodiments, the compound of formula (I) is administered at a rate of about 0.40 mg/kg/hour, and the terminal half-life is about 2 to about 8 hours, about 3 to about 7 hours, about 3.2 to about 6.7 hours, about 3.4 to about 6.5 hours, about 3.6 to about 6.3 hours, about 3.8 to about 6.1 hours, about 4.0 to about 5.9 hours, about 4.2 to about 5.7 hours, about 4.4 to about 5.5 hours, about 4.6 to about 5.3 hours, or about 4.8 to about 5.1 hours.

In certain embodiments, the compound of formula (I) is administered at a rate of about 1.0 mg/kg/hour, and the terminal half-life is about 3 to about 9 hours, about 3.3 to about 8.7 hours, about 3.6 to about 8.2 hours, about 3.8 to about 8.0 hours, about 4.0 to about 7.8 hours, about 4.2 to about 7.6 hours, about 4.4 to about 7.4 hours, about 4.6 to about 7.2 hours, about 4.8 to about 7.0 hours, about 5.0 to about 6.8 hours, about 5.2 to about 6.6 hours, about 5.4 to about 6.4 hours, about 5.6 to about 6.2 hours, or about 5.8 to about 6.0 hours.

In certain embodiments, plasma concentration of the compound of formula (I) increases over time.

In certain embodiments, the time to maximum plasma concentration ($t_{max}$) is about 2 to about 8 hours, about 3 to about 5 hours, about 3.2 to about 4.7 hours, about 3.5 to about 4.5 hours, or about 3.8 to 4.2 hours.

In certain embodiments, the mean peak plasma concentration ($C_{max}$) is about 200 to about 2500 ng/mL, about 500 to about 2000 ng/mL, or about 1000 to about 1500 ng/mL.

In certain embodiments, the compound of formula (I) is administered at a rate of about 2.0 mg/kg/hr for 20 minutes followed by 1.1 mg/kg/hour for 250 minutes, and has a mean peak plasma concentration ($C_{max}$) of about 500 to about 2500 ng/mL, about 1000 to about 2000 ng/mL, about 1050 to about 1950 ng/mL, about 1100 to about 1900 ng/mL, about 1150 to about 1850 ng/mL, about 1200 to about 1800 ng/mL, about 1250 ng/mL to about 1750 ng/mL, about 1300 ng/mL to about 1700 ng/mL, about 1350 to about 1650 ng/mL, or about 1400 ng/mL to about 1500 ng/mL.

In certain embodiments, the compound of formula (I) has a mean $AUC_{inf}$ of about 1000 to about 15,000 ng*h/mL, about 2000 to about 12,500 ng*h/mL, about 3000 to about 10,000 ng*h/mL, or about 5000 to about 8000 ng*h/mL.

In certain embodiments, the compound of formula (I) is administered at a rate of about 2.0 mg/kg/hr for 20 minutes followed by 1.1 mg/kg/hour for 250 minutes and has a mean (±SD) $AUC_{inf}$ of about 5000 to about 15,000 ng*h/mL, about 6200 to about 11,000 ng*h/mL, about 6300 to about 10,900 ng*h/mL, about 6400 to about 10,800 ng*h/mL, about 6500 to about 10,700 ng*h/mL, about 6600 to about 10,600 ng*h/mL, about 6700 to about 10,500 ng*h/mL, about 6800 to about 10,400 ng*h/mL, about 6900 to about 10,300 ng*h/mL, about 7000 to about 10,200 ng*h/mL, about 7100 to about 10,100 ng*h/mL, about 7200 to about 10,000 ng*h/mL, about 7300 to about 9,900 ng*h/mL, about 7400 to about 9800 ng*h/mL, about 7500 to about 9700 ng*h/mL, about 7600 to about 9600 ng*h/mL, about 7700 to about 9500 ng*h/mL, about 7800 to about 9400 ng*h/mL, about 7900 to about 9300 ng*h/mL, about 8000 to about 9200 ng*h/mL, about 8100 to about 9100 ng*h/mL, about 8200 to about 9000 ng*h/mL, about 8300 to about 8900 ng*h/mL, about 8400 to about 8800 ng*h/mL, or about 8500 to about 8700 ng*h/mL.

In certain embodiments, a geometric mean $C_{av30\text{-}3270\ min}$ (average arterial plasma concentration during 30-270 min) is about 200 ng/mL to about 2000 ng/mL, 250 ng/mL to about 1800 ng/mL, about 300 ng/mL to about 1500 ng/mL, or about 350 ng/mL to about 1200 ng/mL.

In certain embodiments, the compound of formula (I) is administered at a rate of about 2.0 mg/kg/hr for 20 minutes followed by 1.1 mg/kg/hour for 250 minutes and has a geometric mean $C_{av30\text{-}3270\ min}$ (average arterial plasma concentration during 30-270 min) of about 800 ng/mL to about 1800 ng/mL, about 900 ng/mL to about 1600 ng/mL, about 1000 ng/mL to about 1500 ng/mL, about 1050 to about 1450 ng/mL, about 1100 to about 1400 ng/mL, about 1150 to about 1350 ng/mL, or about 1200 to about 1300 ng/mL.

In certain embodiments, the compound of formula (I) is administered at a rate of about 2.0 mg/kg/hr for 20 minutes followed by 0.4 mg/kg/hour for 250 minutes and has a geometric mean $C_{av30\text{-}3270\ min}$ (average arterial plasma concentration during 30-270 min) of about 200 ng/mL to about 800 ng/mL, about 250 ng/mL to about 600 ng/mL about 300 ng/mL to about 400 ng/mL, about 310 to about 390 ng/mL, about 320 to about 380 ng/mL, about 330 to about 370 ng/mL, or about 340 to about 360 ng/mL.

In certain embodiments, the compound of formula (I) is administered at a rate of about 2.0 mg/kg/hr for 20 minutes followed by 0.4 mg/kg/hour for 250 minutes and has a mean $C_{max}$ of about 200 to about 800 ng/mL about 375 to about 550 ng/mL, about 400 to about 525 ng/mL, or about 425 to about 500 ng/mL.

In certain embodiments, the compound of formula (I) is administered at a rate of about 2.0 mg/kg/hr for 20 minutes followed by 0.4 mg/kg/hour for 250 minutes and has a mean $AUC_{inf}$ of about 1000 to about 4000 ng*h/mL, about 1500 to about 3500 ng*h/mL, about 2000 to about 3300 ng*h/mL, about 2200 to about 3000 ng*h/mL, or about 2500 to about 2800 ng*h/mL.

In certain embodiments, the average concentration (e.g., Cmax) at a time period (e.g., Tmax of the compound of formula (I) increases with increasing dosing of the surgical anesthetic. In certain embodiments, the increase is at least about 5%, at least about 10%, at least about 25%, at least about 35%, at least about 45%, or about 5% to about 50%, or about 10% to about 40% or about 15% to about 35%.

In certain embodiments, a mean minute ventilation increases during hypoxic measurement. In some embodiments, the mean minute ventilation may increase by at least about 5%, at least about 10%, at least about 25%, at least about 40%, at least about 50%, at least about 60%, at least about 70%, at least about 80%, at least about 90%, at least about 100%, at least about 125%, at least about 150%, or at least about 200%, or any value therein. In some embodiments, the mean minute ventilation may increase by about 5% to about 200%, about 15% to about 175%, about 25% to about 150%, about 50% to about 125%, or about 75% to about 100%.

In certain embodiments, a mean tidal volume increases during hypoxic measurements. In some embodiments, the mean tidal volume may increase by at least about 5%, at least about 10%, at least about 25%, at least about 40%, at least about 50%, at least about 60%, at least about 70%, at least about 80%, at least about 90%, at least about 100%, at least about 125%, at least about 150%, or at least about 200%, or any value therein. In some embodiments, the mean tidal volume may increase by about 5% to about 200%, about 15% to about 175%, about 25% to about 150%, about 50% to about 125%, or about 75% to about 100%.

In certain embodiments, a respiratory rate increases during hypoxic measurements. In some embodiments, the respiratory rate may increase by at least about 5%, at least about 10%, at least about 25%, at least about 40%, at least about 50%, at least about 60%, at least about 70%, at least about 80%, at least about 90%, at least about 100%, at least about 125%, at least about 150%, or at least about 200%, or any value therein. In some embodiments, the respiratory rate may increase by about 5% to about 200%, about 15% to about 175%, about 25% to about 150%, about 50% to about 125%, or about 75% to about 100%.

Composition

In certain embodiments, the instant disclosure is directed to a pharmaceutical composition comprising an effective amount a compound selected from Formula (I) as disclosed herein to treat respiratory depression modulated by a non-opioid agent.

In certain embodiments, the active agent(s) in the pharmaceutical composition is/are lyophilized.

In certain embodiments, the pharmaceutical composition is pre-mixed (e.g., an active agent is pre-mixed with one or more pharmaceutically acceptable excipients and optionally with one or more additional active agents).

In certain embodiments, the pharmaceutical composition may be contained in a glass container or in a plastic container.

In certain embodiments, the pharmaceutical composition further comprises one or more pharmaceutically acceptable excipient. Suitable pharmaceutically acceptable excipients may vary based on the final form and route of administration of the composition.

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, intraperitoneal, intrathoracic, intrapleural and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

In certain embodiments, pharmaceutically acceptable excipients include a pharmaceutically acceptable carrier, such as, a liquid or solid filler, stabilizer, dispersing agent, suspending agent, diluent, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like.

Examples of preservatives useful in accordance with the invention included but are not limited to those selected from the group consisting of benzyl alcohol, sorbic acid, parabens, imidurea and combinations thereof.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

In certain embodiments, the one or more additional excipients includes a pH adjusting agent, which may be selected from sodium hydroxide, potassium hydroxide, calcium hydroxide, ammonium hydroxide, sulfuric acid, phosphoric acid, nitric acid, sodium citrate, sodium acetate, magnesium hydroxide, citric acid, hydrochloric acid, or a mixture thereof.

In certain embodiments, the composition may include one or more additional excipients, such as, without limitations, carbohydrates, antioxidants, chelating agents, low-molecular weight proteins, high-molecular weight polymers, gel-forming agents, stabilizers, additives, wetting agents, emulsifying agents, surfactant and/or dispersing agents, alkalizing agents, coloring agents, synthetic dies, fillers, diluents, mineral oxides, preservatives, or a mixture thereof.

In certain embodiment, the composition further includes an antioxidant. In certain embodiments, the antioxidant may include trivalent phosphorous like e.g phosphite, phenolic antioxidants, hydroxylamines, lactones such as substituted benzofuranones. Hindered phenols, thiosynergists and/or hindered amines are useful for the long-term stability for polymers, whereas the following antioxidants are suitable for use also in situation where the active substance is subject to oxidation: acids (ascorbic acid, erythorbic acid, etidronic acid, gallic acid, hypophosphorous acid, nordihydroguaiaretic acid, propionic acid etc.), phenols (e.g. BHA, BHT, t-butyl hydroquinone, dodecyl gallate, octyl gallate, 1,3,5-trihydroxybenzene), organic and inorganic salts (calcium ascorbate, sodium ascorbate, sodium bisulphite, sodium metabisulfite, sodium sulfite, potassium bisulphite, potassium metabisulphite), esters (calcium ascorbate, dilauryl thiodipropionate, dimyristyl thiodipropionate, distearyl thiodipropionate), pyranon (maltol), and vitamin E (tocopherol, D-α-tocopherol, DL-α-tocopherol, tocopherol acetate, d-α-tocopheryl acetate, dl-α-tocopheryl acetate. However, other anti-oxidative agents known in the art may be used according to the present invention.

In certain embodiments, suitable antioxidants may include, without limitations, sterically hindered phenols, aryl amines, thioureas, thiocarbamates, phosphites, thioether esters, and combinations of the foregoing. Other suitable examples of antioxidants include, but are not limited to, alkylated monophenols, including but not limited to, 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4, 6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1-yl)phenol and mixtures thereof, alkylthiomethylphenols, including but not limited to, 2,4-dioctylthiornethyl-6-tert-hutylphenol, 2,4-dioctylthiomethyl-6-methylphenol, 2,4-dioetylthiomethyl-6-ethylphenol, 2,6-di-dodecylthiornethyl-4-nonylphenol, hydroquinones and alkylated hydroquinones, including but not limited to, 2,6-di-tert-hutyl-4-methoxyphenol, 2,5-di-tert-butylhydroquinone, 2,5-di-tort-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate, tocopherols, including but not limited to, α-tocopherol, β-tocopherol, γ-tocopherol, 8-tocopherol and mixtures thereof (vitamin E), hydroxylated thiodiphenyl ethers, including but not limited to, 2,2'-thiobis(6-tort-butyl-4-methylphenol), 2,2'-thiobis(4-oetylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide, alkylidenebisphenols, including but not limited to, 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis (4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-test-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,5,5-tetra-(5-tert-butyl-4-hydroxy-2-methylphenyl)pentane, O-, N- and S-benzyl compounds, including but not limited to, 3,5,3',5'-tetra-tert-butyl.-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate, hydroxybenzylated malonates, including but not limited to, dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate, aromatic hydroxybenzyl compounds, including but not limited to, 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol, triazine compounds, including but not limited to, 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxy-phenylpropionyl)-hexahydro-1,3,5-triazine, 1,3,5-tris(3,5-dicyclohexyl-4-hydroxybenzyl)iso-cyanurate, benzylphosphonates, including but not limited to, dimethyl-2,5-di-tert-butyl-4-hydroxybenzylphosphonate, diethyl-3,5-di-tert-butyl-4-hydroxybenzylphosphonate, dioctadecyl3,5-di-tent-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid, acylaminophenols, including but not limited to, 4-hydroxylauranilide, 4-hydroxystearanilide, octyl N-(3,5-di-tert-butyl-4-hydroxyphenyl)carbamate, esters of β-(3,5-di-tert-butyl-4-hydroxyphenyl)propionic acid with mono- or polyhydric alcohols, e.g. with methanol, ethanol n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane, esters of 6-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycal, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, amides of 6-(3,5-di-tert-butyl-4-hydroxyphenyl)propionic acid e.g. N,N'-bis(3,5-di-tert-butylA-hydroxyphenylpropionyl) hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal), ascorbic acid (vitamin C), aminic antioxidants, including but not limited to, N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(I-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, including but not limited to, p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated teak-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene, and combinations of the foregoing.

In certain embodiments, suitable pharmaceutically acceptable excipients may include acrylics, cellulose derivatives, polysaccharides, monosaccharides, gums, natural or synthetic polymers (e.g., polyalkylene oxides (e.g., polymethylene oxides, polyethylene oxides, polypropylene oxides) polyethylenes, polypropylenes, polyvinyl chlorides, polycarbonates, polystyrenes, polyacrylates, polycaprolactone, polymethacrylates copolymers thereof, and mixtures thereof), liposomes, disintegrants (e.g., polyvinylpyrrolidone, sodium starch glycolate, crosscarmellose sodium, or a mixture thereof), glidants, lubricants, absorption enhancers, surfactants, binders, softeners, plasticizers (e.g., lecithin, hydrogenated vegetable oils, glycerol ester, lanolin, methyl ester, pentaerythritol ester, rice bran wax, stearic acid, sodium potassium stearates, and the like), waxes, fats, emulsifiers, fillers, antioxidants, flavors, colorants, diluents, processing aids (e.g., granulating aids), sweeteners such as those described above with respect to the chewable composition, fixing agents (e.g., polyols such as, without limitations, sorbitol, maltitol/isomalt, mannitol, starch, and the like), pH-adjusting agents, viscosity adjusting agents, solubility increasing or decreasing agents, osmotic agents, solvents, or a combination thereof.

In certain embodiments, suitable pharmaceutically acceptable excipients may include polyvinylpyrrolidone, natural and synthetic gums, polyvinyl alcohol, corn starch, hydrophilic and hydrophobic materials such as sustained release polymers, acrylic resins, protein-derived materials, waxes, shellacs, and solid or semi-solid oils such as hydrogenated castor oil and hydrogenated vegetable oil. More specifically, the controlled release materials can be, e.g., alkylcelluloses such as ethylcellulose, acrylic and methacrylic acid polymers and copolymers (e.g., acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid) (anhydride), methyl methacrylate, polymethacrylate, poly(methyl methacrylate), poly(methyl methacrylate) copolymer, polyacrylamide, aminoalkyl methacrylate copolymer, poly(methacrylic acid anhydride), glycidyl methacrylate copolymers, and mixtures of any of the foregoing), and cellulose ethers, such as hydroxyalkylcelluloses (e.g., hydroxypropylmethylcellulose) and carboxyalkylcelluloses. Waxes include, e.g., natural and synthetic waxes, fatty acids, fatty alcohols, and mixtures of the same (e.g., beeswax, carnauba wax, stearic acid and stearyl alcohol).

In certain embodiments, suitable pharmaceutically acceptable excipients may include gelling agents, such as and without limitation, sugars or sugar derived alcohols, such as mannitol, sorbitol, and the like, starch and starch derivatives, cellulose derivatives (such as microcrystalline cellulose, sodium carboxymethyl cellulose, methylcellulose, ethyl cellulose, hydroxyethyl cellulose, hydroxypropyl cellulose, hydroxypropyl methylcellulose, cellulose esters, cellulose diesters, cellulose triesters, cellulose ethers, cellulose ester-ethers, cellulose acylates, cellulose diacylates, cellulose triacylates, cellulose acetates, cellulose diacetates, cellulose triacetates, cellulose acetate propionates, cellulose acetate butyrates, cellulose acetate succinate, cellulose acetate phthalate, hydroxypropyl methyl cellulose phthalate, hydroxy propyl methyl cellulose acetate succinate (hypermellose acetate succinate), and mixtures thereof), attapulgites, bentonites, dextrins, alginates, algenic acid salts such as sodium alginate and potassium alginate, casein, stearic acid, shellac, carrageenan, gum tragacanth, gum acacia, gum arabic, pullulan gum, dextrin, gellan gum, agar gum, tara gum, karaya, guar gum, welan gum, rhamsan gum, locust bean gum, xanthan gum, pectin, gelatin, kaolin, lecithin, magnesium aluminum silicate, the carbomers and carbopols, polyvinylpyrrolidone, polyethylene glycol, polyethylene oxide, polyvinyl alcohol, silicon dioxide, surfactants, mixed surfactant/wetting agent systems, emulsifiers, other polymeric materials, and mixtures thereof.

In certain embodiments, suitable pharmaceutically acceptable excipients may include hydrophilic excipients, such as without limitations, water, low molecular weight polyols, such as, polyethylene glycol, polypropylene glycol, or a combination thereof. Examples of other suitable hydrophilic carriers include, without limitations, polyoxyethylene derivatives of a sorbitan ester, such as sorbitan monolaurate (Polysorbate 20), Polysorbate 80, Polysorbate 60, polyoxyethylene 20 sorbitan trioleate (Polysorbate 85), acetic acid, formic acid, other hydrophilic surfactants and mixtures thereof. Exemplary low molecular weight polyols include, without limitations, those having a number average molecular weight of from any of about 200 Dalton, about 400 Dalton, about 600 Dalton, about 800 Dalton, or about 1000 Dalton to any of about 2000 Dalton, about 3000 Dalton, about 4000 Dalton, about 5000 Dalton, about 6000 Da, or about 7000 Da, or any sub-range or single value therein (for instance, polyethylene glycol 400, polyethylene glycol 600, or the like).

In certain embodiments, suitable pharmaceutically acceptable excipients may include plasticizers, such as, but not be limited to, sugar alcohol plasticizer such as triacetin, isomalt, maltitol, xylitol, erythritol, adonitol, dulcitol, pentaerythritol, or mannitol; or polyol plasticizer such as diglycerin, ethylene glycol, diethylene glycol, triethyleneglycol, tetraethylene glycol, dipropylene glycol, a polyethylene glycol up to 10,000 MW, neopentyl glycol, propylene glycol, 1,3-propanediol, 2-methyl-1,3-propanediol, trimethylolpropane, a polyether polyol, ethanol amines; and mixtures thereof. Other exemplary plasticizers may also include, without limitations, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, citrate ester-type plasticizers, and triacetin. Such plasticizers may include 1,2-butylene glycol, 2,3-butylene glycol, styrene glycol, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, glyceryl monostearate, polysorbate 80, acetyl triethyl citrate, tributyl citrate and allyl glycolate, and mixtures thereof.

In certain embodiments, suitable pharmaceutically acceptable excipients may include plasticizer such as, without limitations, phosphate esters; phthalate esters; amides; mineral oils; fatty acids and esters; fatty alcohols, vegetable oils and hydrogenated vegetable oils including acetylated hydrogenated cottonseed glyceride and acetylated hydrogenated soybean oil glycerides; acetyl tributyl citrate, acetyl triethyl citrate, Castor oil, diacetylated monoglycerides, dipropylene glycol salicylate glycerin, glyceryl cocoate, mono- and di-acetylated monoglycerides, nitrobenzene, carbon disulfide, fl-naphtyl salicylate, phthalyl glycolate, diocyl phthalate; sorbitol, sorbitol glyceryl tricitrate; sucrose octaacetate; α-tocopheryl polyethylene glycol succinate, phosphate esters; phthalate esters; amides; mineral oils; fatty acids and esters; fatty alcohols; and vegetable oils, fatty alcohols including cetostearyl alcohol, cetyl alcohol, stearyl alcohol, oleyl alcohol and myristyl alcohol; methyl abietate, acetyl tributyl citrate, acetyl triethyl citrate, diisooctyl adipate, amyl oleate, butyl ricinoleate, benzyl benzoate, butyl and glycol esters of fatty acids, butyl diglycol carbonate, butyl oleate, butyl stearate, di(beta-methoxyethyl) adipate, dibutyl sebacate, dibutyl tartrate, diisobutyl adipate, dihexyl adipate, triethylene glycol di(beta-ethyl butyrate), polyethylene glycol di(2-ethyl hexoate), diethylene glycol monolaurate, monomeric polyethylene ester, hydrogenated methyl ester of rosin, methoxyethyl oleate, butoxyethyl stearate, butyl phthalyl butyl glycolate, glycerol tributyrate, triethylene glycol dipelargonate, beta-(p-tert-amyl phenoxy) ethanol, beta(p-tert-butytphenoxy)ethanol, beta-(p-tert-butytphenoxyethyl)acetate, bis(beta-p-tert-buthylphenoxydiethyl)ether, camphor, Cumar W-1, Cumar MH-1, Cumar V-1, diamyl phthalate, (diamylphenoxy) ethanol, diphenyl oxide, technical hydroabietyl alcohol, beckolin, benzene hexahydrochlonde, Clorafin 40, Piccolastic A-5, Piccalastic A-25, Flexol B-400, Glycerol alfa-methyl alfaphenyl ether, chlorinated naphthalene, HB-40, monoamylphthalate. Nevillac 10 o-nitrodiphenyl and Paracril 26.

In certain embodiments, suitable pharmaceutically acceptable excipients may include plasticizer such as, without limitations, sugar alcohol plasticizer such as isomalt, maltitol, sorbitol, xylitol, erythritol, adonitol, dulcitol, pentaerythritol, or mannitol; or polyol plasticizer such as glycerin, diglycerin, ethylene glycol, diethylene glycol, triethyleneglycol, tetraethylene glycol, dipropylene glycol, a polyethylene glycol up to 10,000 MW, neopentyl glycol, propylene glycol, 1,3-propanediol, 2-methyl-1,3-propanediol, trimethylolpropane, a polyether polyol, ethanol amines; and mixtures thereof. Other exemplary plasticizers may include, without limitations, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, citrate ester-type plasticizers, and triacetin. Such plasticizers may include 1,2-butylene glycol, 2,3-butylene glycol, styrene glycol, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, glyceryl monostearate, polysorbate 80, acetyl triethyl citrate, tributyl citrate and allyl glycolate, and mixtures thereof.

In certain embodiments, suitable pharmaceutically acceptable excipients may include fragrances such as, without limitations, natural and/or synthetic fragrance raw materials. For instance, oil soluble perfume oils, which may or may not be in mixture with water soluble perfume oils. Oil soluble perfume materials are natural, or natural-identical essential oils such as orange oil, lavender oil, pine oil, eucalyptus oil, lemon oil, clove leaf, peppermint oil, cedarwood oil, rosemary oil, bergamot oil, lavandin oil, patchouli oil, chamomile oil, jasmine oil, spike oil, rose oil, Vetiver oil, fennel oil, anise oil, thyme oil, germanium oil, menthol, and marjoram oil. An animal fragrance is for example musk, castoreum, aber or zibet. Spagyric essences are also known in the art. They are made by fermenting certain herbs that are then processed to the final product. Synthetic fragrance ingredients are for example synthetic essential oils such as composed of single compounds such as linalol, terpineol, nerol, citronellal, benzaldehyde, cinnamon aldehyde, vanillin, ethylvanillin, or methylacetophenone. The fragrance materials may also be synthetic oil soluble perfume oils selected from the usual group consisting of fragrant hydrocarbons, alcohols, ketones, aldehydes, ethers, esters, polyene derivatives. Other fragrances that may be used are catalogued and described in references and databases such as S. Arctander, Perfume and Flavor Chemicals, Volumes I and II (1960, 1969; reprint 2000); Allured's Flavor and Fragrance Materials (2005); and database maintained by the Research Institute for Fragrance Materials at www.rifm.org.

In certain embodiments, suitable pharmaceutically acceptable excipients may include a perfume oil. Suitable perfume oils include mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamom, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl-methylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include mainly the terpenes and balsams.

In certain embodiments, suitable pharmaceutically acceptable excipients may include essential oils of relatively low volatility, which are mostly used as aroma components, are also suitable as perfume oils, e.g. sage oil, chamomile oil, oil of cloves, melissa oil, mint oil, cinnamon leaf oil, linden blossom oil, juniper berry oil, vetiver oil, olibanum oil, galbanum oil, labolanum oil and lavandin oil. Other suitable oils include bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

In certain embodiments, suitable pharmaceutically acceptable excipients may include preservatives. The term "preservative", as used herein, refers to an agent that extends the storage life of the dosage form by retarding or preventing deterioration of flavor, odor, color, texture, appearance, therapeutic value, or safety. A preservative need not provide a lethal, irreversible action resulting in partial or complete microbial cell destruction or incapacitation. Sterilants, sanitizers, disinfectants, sporicides, viracides and tuberculocidal agents provide such an irreversible mode of action, sometimes referred to as "bactericidal" action. In contrast, a preservative can provide an inhibitory or bacteriostatic action that is reversible, in that the target microbes can resume multiplication if the preservative is removed. The principal differences between a preservative and a sanitizer primarily involve mode of action (a preservative prevents growth rather than killing microorganisms) and exposure time (a preservative has days to months to act whereas a sanitizer has at most a few minutes to act). Suitable preservatives include, without limitations, phenoxyethanol, a solution of paraben, pentanediol and sorbic acid, as well as silver complexes.

In certain embodiments, suitable pharmaceutically acceptable excipients may include coloring agents, such as, without limitations, colors such as e.g., white, black, yellow, blue, green, pink, red, orange, violet, indigo, and brown.

In certain embodiments, suitable pharmaceutically acceptable excipients may include, without limitations, "flavor extract" obtained by extracting a part of a raw material, e.g., animal or plant material, often by using a solvent such as ethanol or water; natural essences obtained by extracting essential oils from the blossoms, fruit, roots, etc., or from the whole plants. Additional exemplary flavoring agents for the compositions described herein may include, but not be limited to, menthol, spearmint, and cinnamon, coffee beans, other flavors or fragrances such as fruit flavors (e.g., cherry, orange, grape, etc.), quaternary ammonium bases. The effect of flavors may be enhanced using flavor enhancers like tartaric acid, citric acid, vanillin, or the like.

In certain embodiments, suitable pharmaceutically acceptable excipients may include sweetening agents such as, without limitations, one or more artificial sweeteners, one or more natural sweeteners, or a combination thereof. Artificial sweeteners include, e.g., acesulfame and its various salts such as the potassium salt (available as Sunett®), alitame, aspartame (available as NutraSweet® and Equal®), salt of aspartame-acesulfame (available as Twinsweet®), neohesperidin dihydrochalcone, naringin dihydrochalcone, dihydrochalcone compounds, neotame, sodium cyclamate, saccharin and its various salts such as the sodium salt (available as Sweet'N Low®), *Stevia*, chloro derivatives of sucrose such as sucralose (available as Kaltame® and Splenda®), and mogrosides. Natural sweeteners include, e.g., glucose, dextrose, invert sugar, fructose, sucrose, glycyrrhizin; monoammonium glycyrrhizinate (sold under the trade name MagnaSweet®); *Stevia rebaudiana* (Stevioside), natural intensive sweeteners, such as Lo Han Kuo, polyols such as sorbitol, mannitol, xylitol, erythritol, and the like.

In certain embodiments, suitable pharmaceutically acceptable excipients may include alkalizing agent(s), such as, without limitations, magnesium oxide, ammonium hydroxide, sodium hydroxide, sodium carbonate, sodium citrate, trisodium phosphate and/or disodium phosphate.

In certain embodiments, suitable pharmaceutically acceptable excipients may include lubricant(s)/release agent (s) such as, but not limited to, fatty acids and their salts, fatty alcohols, fatty esters, fatty amines, fatty amine acetates and fatty amides. Other suitable lubricants may include, but not be limited to, glyceryl behenate (Compritol™ 888), metallic stearates (e.g., magnesium, calcium and sodium stearates), stearic acid, hydrogenated vegetable oils (e.g., Sterotex™), talc, waxes such as beeswax and carnauba wax, silica, fumed silica, colloidal silica, calcium stearate, long chain fatty alcohols, boric acid, sodium benzoate and sodium acetate, sodium chloride, DL-Leucine, polyethylene glycols (e.g., Carbowax™ 4000 and Carbowax™ 6000), sodium oleate, sodium benzoate, sodium acetate, sodium lauryl sulfate, sodium stearyl fumarate (Pruv™), magnesium lauryl sulfate, stearic acid, stearyl alcohol, mineral oil, paraffin, micro crystalline cellulose, glycerin, propylene glycol and combinations thereof.

In certain embodiments, suitable pharmaceutically acceptable excipients may include diluents such as, but not limited to, lactose USP, lactose USP (anhydrous), lactose USP (spray dried), starch USP, directly compressible starch, mannitol USP, sorbitol, dextrose monohydrate, microcrystalline cellulose NF, dibasic calcium phosphate dihydrate NF, sucrose-based diluents, confectioner's sugar, monobasic calcium sulfate monohydrate, calcium sulfate dihydrate NF, calcium lactate trihydrate granular NF, dextrates NF (e.g., Emdex™), dextrose (e.g., Cerelose™), inositol, hydrolyzed cereal solids such as the Maltrons™ and Mor-Rex™, amylose, powdered cellulose (e.g., Elcema™), calcium carbonate, glycine, bentonite, polyvinylpyrrolidone, and the like.

In certain embodiments, suitable pharmaceutically acceptable excipients may include oils and fats such as, but not be limited to, almond oil, argan oil, avocado oil, canola oil, cashew oil, castor oil, cocoa butter, coconut oil, colza oil, corn oil, cottonseed oil, grape seed oil, hazelnut oil, hemp oil, hydroxylated lecithin, lecithin, linseed oil, macadamia oil, mango butter, manila oil, mongongo nut oil, olive oil, palm kernel oil, palm oil, peanut oil, pecan oil, perilla oil, pine nut oil, pistachio oil, poppy seed oil, pumpkin seed oil, rice bran oil, safflower oil, sesame oil, shea butter, soybean oil, sunflower oil, walnut oil, and watermelon seed oil. Other oil and fats that may be in the fill of the PVA shell may include, but not be limited to, fish oil (omega-3), crill oil, animal or vegetable fats, e.g., in their hydrogenated form, mono-, di-, and tri-glycerides with C12-, C14-, C16-, C18-, C20- and C22-fatty acids.

In certain embodiments, suitable pharmaceutically acceptable excipients may include vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses hydroxyalkylcelluloses and hydroxyalkylalkylcelluloses, such as methylcelulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids, polyacrylamides, and polyacrylic acid esters, polymethacrylic acids, polymethacrylamides, and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water-soluble chemical derivatives of starch, cationically modified acrylates and methacrylates possessing, for example, a tertiary or quaternary amino group, such as the diethylaminoethyl group, which may be quaternized if desired; and other similar polymers; inorganic fillers, such as the oxides of magnesium aluminum, silicon, titanium, etc.

In certain embodiments, suitable pharmaceutically acceptable excipients may include a hydrophobic material, including, but not limited to, digestible, long chain ($C_8$-$C_{50}$, especially $C_{12}$-$C_{40}$), substituted or unsubstituted hydrocarbons, such as natural or synthetic waxes (such as beeswax, glycowax, castor wax and carnauba wax), fatty alcohols (such as lauryl, myristyl, stearyl, cetyl or preferably cetostearyl alcohol), fatty acids, including, but not limited to, mono-diglyceride of medium chain fatty acids (such as caprylic, capric, caproic, lauric, oleic, linoleic), medium chain triglycerides, fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones.

In certain embodiments, suitable pharmaceutically acceptable excipients may include polyvinyl alcohols, polyvinyl pyrrolidone, polyalkylene oxides, polyacrylic acid, cellulose, cellulose ethers, cellulose esters, cellulose amides, polyvinyl acetates, polycarboxylic acids and salts, acetic acid, caprylic acid, oleic acid, polyaminoacids or peptides, polyamides, polyacrylamide, copolymers of maleic/acrylic acids, polysaccharides including starch and gelatin, natural gums such as xanthan, and carrageenans. For example, polymers can be selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and combinations thereof, or selected from polyvinyl alcohols, polyvinyl alcohol copolymers and hydroxypropyl methyl cellulose (HPMC), methacrylic acid/methyl methacrylate, methacrylic acid/ethyl acrylate copolymers, methacrylic acid/methyl acrylate/methyl methacrylate copolymers, shellac, hydroxypropyl methylcellulose phthalate, hydroxyl propyl methyl cellulose acetate succinate, hydroxypropyl methyl cellulose trimellitate, cellulose acetate phthalates, polyvinyl acetate phthalates, PEG-35 castor oil, caprylocaproyl polyoxyl-8 glycerides, glyceryl distearate, and combinations thereof.

In certain embodiments, suitable pharmaceutically acceptable excipients may include high HLB surfactants such as, without limitations, polysorbate 80-polyoxyethylene (20) sorbitan monooleate, polyoxyl 40 hydrogenated castor oil, polyoxyl 35 castor oil, caprylocaproyl macrogol glycerides, and combinations thereof.

In certain embodiments, suitable pharmaceutically acceptable excipients may include fillers such as, without limitations, lactose, microcrystalline cellulose, and combinations thereof.

In certain embodiments, suitable pharmaceutically acceptable excipients may include natural gums (e.g., a natural plant gum). Suitable natural gums include, without limitations, guar gum, carob gum, konjac gum, xanthan gum, sclerotium gum, acacia gum, cellulose gum (modified or not), or a combination thereof.

In certain embodiments, suitable pharmaceutically acceptable excipients may include emulsifiers such as, without limitations, PEG-30 Dipolyhydroxystearate, PEG-4 Dilaurate, PEG-8 Dioleate, PEG-40 Sorbitan Peroleate, PEG-7 Glyceryl Cocoate, PEG-20 Almond Glycerides, PEG-25 Hydrogenated Castor Oil, Glyceryl Stearate (and) PEG-100 Stearate, PEG-7 Olivate, PEG-8 Oleate, PEG-8 Laurate, PEG-60 Almond Glycerides, PEG-20 Methyl Glucose Sesquistearate, PEG-40 Stearate, PEG-100 Stearate, PEG-80 Sorbitan Laurate, Steareth-2, Steareth-12, Oleth-2, Ceteth-2, Laureth-4, Oleth-10, Oleth-10/Polyoxyl 10 Oleyl Ether, Ceteth-10, Isosteareth-20, Cetareth-20, Oleth-20, Steareth-20, Steareth-21, Ceteth-20, Isoceteth-20, Laureth-23, Steareth-100, Glyceryl Stearate Citrate, Glyceryl Stearate SE (self-emulsifying), stearic acid, salts of stearic acid, polyglyceryl-3-methylglycosedistearate, or a combination thereof.

Further suitable emulsifiers are phosphate esters and the salts thereof such as cetyl phosphate (Amphisol® A), diethanolamine cetyl phosphate (Amphisol®DEA), potassium cetyl phosphate (Amphisol® K), sodium cetearyl sulfate, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, Cetearyl Glucoside, Lauryl Glucoside, Decyl Glucoside, Sodium Stearoyl Glutamate, Sucrose Polystearate and Hydrated Polyisobutene. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof.

In certain embodiments, suitable pharmaceutically acceptable excipients may include chelating agents such as, without limitations, disodium ethylenediaminetetraacetic acid (EDTA), diethylenetriaminepentaacetic acid (DTPA), N-(hydroxyethyl)-ethylenediaminetriacetic acid (HEDTA), and nitrilotriacetic acid (NTA).

In certain embodiments, suitable pharmaceutically acceptable excipients may include fatty alcohols, such as, without limitations guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of C12-C15 alcohols, acetylated lanolin alcohol, etc.

In certain embodiments, suitable pharmaceutically acceptable excipients may include esters of fatty acids, such as, without limitations esters of linear $C_6$-$C_{24}$ fatty acids with linear $C_3$-$C_{24}$ alcohols, esters of branched $C_6$-$C_{13}$carboxyl acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerization of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerization of unsaturated fatty alcohols). Additional suitable examples of ester oils are isopropyl myristate, isopropyl palmitate, isopropyl stearate, isopropyl isostearate, isopropyl oleate, n-butyl stearate, n-hexyl laurate, n-decyl oleate, isooctyl stearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

In certain embodiments, suitable pharmaceutically acceptable excipients may include other adjuvants, such as, without limitations, diethylhexyl 2,6-naphthalate, di-n-butyl adipate, di(2-ethylhexyl)-adipate, di(2-ethyl hexyl)-succinate and diisotridecyl acelaat, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$ dicarboxylic acids with linear or branched alcohols having from 1 to 22 carbon atoms or polyols having from 2 to 10 carbon atoms and from 2 to 6 hydroxy groups.

In certain embodiments, suitable pharmaceutically acceptable excipients may include natural or synthetic triglycerides (including glyceryl esters and derivatives), such as, without limitations, di- or triglycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borage oil, etc. Additional suitable excipients include waxes including esters of long-chain acids and alcohols as well as compounds having wax-like properties, e.g., carnauba wax, beeswax (white or yellow), lanolin wax, candelilla wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

In certain embodiments, suitable pharmaceutically acceptable excipients may include pearlescent waxes, such as, without limitations, alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially lauryl and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

In certain embodiments, suitable pharmaceutically acceptable excipients may include hydrocarbon oils, such as, without limitations, mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

In certain embodiments, suitable pharmaceutically acceptable excipients may include silicones or siloxanes (organosubstituted polysiloxane), such as, without limitations, dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

In certain embodiments, suitable pharmaceutically acceptable excipients may include emulsifiers, such as, without limitations, carboxylic acids and their salts: alkaline soap of sodium, potassium and ammonium, metallic soap of calcium or magnesium, organic basis soap such as Lauric, palmitic, stearic and oleic acid etc. Alkyl phosphates or phosphoric acid esters, acid phosphate, diethanolamine phosphate, potassium cetyl phosphate. Ethoxylated carboxylic acids or polyethylene glycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycol ether such as laureth-n, cetaereth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated paraffins, sulfonated tetrapropyene sulfonate, sodium lauryl sulfates, ammonium and ethanolamine lauryl sulfates, lauryl ether sulfates, sodium laureth sulfates, sulfosuccinates, acetyl isothionates, alkanolamide sulfates, taurines, methyl taurines, imidazole sulfates. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block(oxyethylene). Zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethylammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkyl betaine, N-alkylaminobetaines. Alkylimidazolines, alkylopeptides, lipoaminoacides, self-emulsifying bases and the compounds as described in K. F. DePolo, A short textbook of cosmetology, Chapter 8, Table 8-7, p 250-251.

Suitable nonionic bases include, without limitations, PEG-6 beeswax (and) PEG-6 stearate (and) polyglyceryl-2-isostearate, glyceryl stearate (and) PEG-100 stearate, PEG-5 glyceryl stearate, sorbitan oleate (and) polyglyceryl-3 ricinoleate, sorbitan stearate and sucrose cocoate, glyceryl stearate and laureth-23, cetearyl alcohol and ceteth-20, cetearyl alcohol and polysorbate 60 and PEG-150 and stearate-20, cetearyl alcohol and cetearyl polyglucoside, cetearyl alcohol and ceteareth-20, cetearyl alcohol and PEG-40 castor oil, cetearyl alcohol and PEG-40 castor oil and sodium cetearyl sulfate, stearyl alcohol and steareth-7 and steareth-10, cetearyl alcohol and szeareth-7 and steareth-10, glyceryl stearate and PEG-75 stearate, propylene glycol ceteth-3 acetate, propylene glycol isoceth-3 acetate, cetearyl alcohol and ceteth-12 and oleth-12, PEG-6 stearate and PEG-32 stearate, PEG-6 stearate and ceteth-20 and steareth-20, PEG-6 stearate and ceteth-20 and glyceryl stearate and steareth-20, glyceryl stearate and ceteareth-20.

Suitable anionic alkaline bases includes, without limitations, PEG-2 stearate SE, glyceryl stearate SE, propylene glycol stearate. Anionic acid bases such as cetearyl Alcohol and Sodium cetearyl sulfate, cetearyl alcohol and sodium lauryl sulfate, trilaneth-4 phosphate and glycol stearate and PEG-2 stearate, glyceryl stearate and sodium lauryl Sulfate. Cationic acid bases such as cetearyl alcohol and cetrimonium bromide.

In certain embodiments, suitable pharmaceutically acceptable excipients may include adjuvants and additives, such as, without limitations, surfactants, super-fatting agents, consistency regulators, thickeners, polymers, stabilizers, biogenic active ingredients, swelling agents, further UV light-protective factors, antioxidants, hydrotropic agents, preservatives, self-tanning agents, solubilizers, perfume oils, colorants, bacteria-inhibiting agents and the like.

In certain embodiments, suitable pharmaceutically acceptable excipients may include super-fatting agents, such as, without limitations, lanolin and lecithin and also polyethoxylated or acetylated lanolin and lecithin derivatives, polyol fatty acid esters, monoglycerides and fatty acid alkanolamides, the latter simultaneously acting as foam stabilizers.

In certain embodiments, suitable pharmaceutically acceptable excipients may include surfactants, such as, without limitations, fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, .alpha.-olefin sulfonates, ethercarboxylic acids, alkyl oligoglucosides, fatty acid glucamides, alkylamidobetaines and/or protein fatty acid condensation products, the latter preferably being based on wheat proteins.

In certain embodiments, suitable pharmaceutically acceptable excipients may include consistency regulators/thickeners and rheology modifiers, such as, without limitations, silicium dioxide, magnesium silicates, aluminium silicates, polysaccharides or derivatives thereof for example hyaluronic acid, xanthan gum, guar-guar, agar-agar, alginates, carrageenan, gellan, pectines, or modified cellulose such as hydroxycellulose, hydroxypropylmethylcellulose. In addition polyacrylates or homopolymer of reticulated acrylic acids and polyacrylamides, carbomer (CARBOPOL types 980, 981, 1382, ETD 2001, ETD2020, ULTREZ 10) or SALCARE range such as SALCARE SC80 (steareth-10 allyl ether/acrylates copolymer), Salcare SC81 (acrylates copolymer), Salcare SC91 and Salcare AST (sodium acrylates copolymer/PPG-1 trideceth-6), SEPIGEL 305 (polyacrylamide/laureth-7), SIMULGEL NS and SIMULGEL EG (hydroxyethyl acrylate/sodium acryloyldimethyl taurate copolymer), STABILEN 30 (acrylates/vinyl isodecanoate crosspolymer), PEMULEN TR-1 (acrylates/C10-30 alkyl acrylate crosspolymer), LUVIGEL EM (sodium acrylates copolymer), ACULYN 28 (acrylates/beheneth-25 methacrylate copolymer), etc.

In certain embodiments, suitable pharmaceutically acceptable excipients may include polymers, such as, without limitations, an anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylate-tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatized cellulose ethers and silicones. Furthermore, the polymers as described in EP 1093796 (pages 3-8, paragraphs 17-68) may be used.

In certain embodiments, suitable pharmaceutically acceptable excipients may include antioxidants, such as, without limitations amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid phytic acid, lactoferrin), hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the disodium salts), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned.

In certain embodiments, suitable pharmaceutically acceptable excipients may include hydrotropic agents, such as, without limitations, ethoxylated or non-ethoxylated mono-alcohols, diols or polyols with a low number of carbon atoms or their ethers (e.g. ethanol, isopropanol, 1,2-dipropanediol, propylene glycol, glycerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

In certain embodiments, suitable pharmaceutically acceptable excipients may include preservatives, such as, without limitations, Methyl-, Ethyl-, Propyl-, Butyl-parabens, Benzalkonium chloride, 2-Bromo-2-nitro-propane-1,3-diol, Dehydroacetic acid, Diazolidinyl Urea, 2-Dichlorobenzyl alcohol, DMDM hydantoin, Formaldehyde solution, Methyldibromoglutanitrile, Phenoxyethanol, Sodium Hydroxymethylglycinate, Imidazolidinyl Urea, Triclosan and further substance classes listed in the following reference: K. F. DePolo-A short textbook of cosmetology, Chapter 7, Table 7-2, 7-3, 7-4 and 7-5, p 210-219.

In certain embodiments, suitable pharmaceutically acceptable excipients may include bacteria-inhibiting agents, such as, without limitations, 2,4,4'-trichloro-2'-hydroxydiphenyl ether, chlorhexidine (1,6-di(4-chlorophenylbiguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-trimethyl-2,6,10-dodecatrien-1-ol), which is present in lime blossom oil. Glycerol monolaurate has also proved to be a bacteriostatic agent.

Other pharmaceutically acceptable excipients may also be utilized as recognized by those skilled in the art.

In certain embodiments, pharmaceutically acceptable excipients may be included (individually or cumulatively) in the pharmaceutical compositions described herein in a concentration ranging from any of about 5 wt %, about 10 wt %, about 15 wt %, about 20 wt %, about 25 wt %, about 30 wt %, about 35 wt %, about 40 wt %, about 45 wt %, or about 50 wt % to any of about 55 wt %, about 60 wt %, about 65 wt %, about 70 wt %, about 75 wt %, about 80 wt %, about 85 wt %, about 90 wt %, about 95 wt %, or about 99 wt %, or any sub-range or single value therein based on the total weight of the composition.

Method of Preparation

In certain embodiments, the instant disclosure is directed to a method of preparing any of the compositions described herein. In certain embodiments, the method includes combining a therapeutically effective amount of the compounds disclosed herein with one or more pharmaceutically acceptable excipients.

The various compositions described herein may be formulated to have a customized release profile for the active agent, such as, without limitations, an immediate release profile, a controlled release profile, a delayed release profile, an enteric release profile, a zero order release profile, a first order release profile, a pulsatile release profile, a targeted release in a certain location within the body (such as a target location within the gastrointestinal tract), and the like.

EXAMPLES

A study is conducted for Compound A. The study is a 3-period, randomized, placebo-controlled, double-blind, crossover study in healthy subjects. The primary objective of the study was to determine the safety and tolerability of Compound A in healthy participants after low and high doses of Compound A under hypoxic and hypercapnic conditions in conjunction with low and high doses of propofol. Another primary objective of the study was to determine the ventilatory response of low and high doses of Compound A under hypoxic and hypercapnic conditions in conjunction with low and high doses of propofol. A secondary objective of the study was to determine the cardiovascular response of low and high doses of Compound A during hypoxic and hypercapnic conditions in conjunction with low and high doses of propofol. Another secondary objective of the study was to evaluate the ventilatory response after administration of Compound A and propofol, under different ventilatory conditions: hypoxia and hyperoxic exposure at normocapnia followed by the same sequence at hypercapnia. The study was conducted in conformance with Good Clinical Practice. The study was a randomized, double-blinded, placebo-controlled, three-way crossover study to assess the safety, tolerability, respiratory PD, and PK of Compound A in healthy male and female participants. Subjects were initially screened up to 6 weeks prior to randomization. Following successful initial medical screening, they were scheduled for the study and receive a randomization number. Subjects underwent 3 separate treatment periods. In each of these periods, low or high doses of Compound A or placebo were continuously perfused throughout for a period of 270 minutes. During each period, subjects received different intravenous propofol dosages or placebo in set order: placebo—propofol low dose—propofol high dose. Each treatment session of propofol or placebo is 70 minutes. During each propofol treatment session, different ventilatory conditions are applied, hypoxia and hypercapnia (FIG. 1).

In FIG. 1, single assessment periods are displayed with the stepped hypoxic, hyperoxic and hypercapnic regimens indicated by colored lines. Each assessment period (i.e., "run") consists of a hypoxia/hyperoxic exposure at normocapnia followed by one the same sequence at hypercapnia. A total of 12 participants completed all treatments as planned per protocol. The participants received the following treatments in random order during the dosing periods:

Placebo+placebo/propofol low/propofol high/
Compound A low+placebo/propofol low/propofol high
Compound A high+placebo/propofol low/propofol high Subjects were admitted to study site on Day −1 for pre-dose activities and eligibility was reassessed and stayed overnight. On each dosing day (Day 1), subjects were transferred to a special unit at study site in the morning (or early afternoon) after a minimum 8 hour overnight fasting. After placement of the respiratory and cardiovascular monitoring/assessment devices including an arterial line, subjects assumed the semi-recumbent position and sufficient time was allowed for subjects to resume a normal breathing pattern. After completion of baseline evaluations, all measurements were performed as per the schedule of assessments.

Upon completion of all measurements on the dosing day, subjects were monitored overnight and assessed the next morning (at least 12 hours post study treatments) prior to discharge (Day 2). Subjects were not immediately discharged in cases where prolonged care is required (e.g., due to adverse event, residual sedation etc.) and were treated as necessary.

Duration of Treatment: Participation was approximately 10 weeks divided as follows:
Screening: Up to 42 days before first dosing
Treatment phase of approximately 21 days, including three treatment and study assessment periods of 3 days each with approximately 7 days (minimum of 3) between dosing days
Follow up 7 days after last dosing Healthy adult subjects were selected for the study.
The research pharmacist at the study center and an independent statistician will not be blinded to Compound A treatment.

Study Treatment Administered
The investigational product was prepared as follows: Compound A 10 mg/mL was supplied as 50-mL vials (batch number B210239). Infusion bags at a fixed concentration of Compound A ~0.8 mg/mL in Ringer's lactate were prepared for dosing by the LUMC trial pharmacy per the pharmacy manual. Compound A was administered intravenously based on participant weight for a period of 270 minutes. Investigational product was dispensed for each participant according to the randomisation list. A loading dose was administered at 2.0 mg/kg/h for 10 (for low dose) or 20 minutes (for high dose) for both the low and high dose followed by continuous infusion of the following for 250-260 minutes, so that the total infusion time is 270 minutes:
Low dose was a fixed rate of 2 mg/kg/h for 10 minutes followed by 0.4 mg/kg/h for 260 minutes or
High dose was a fixed rate of 2 mg/kg/h for 20 minutes followed by 1.1 mg/kg/h for 250 minutes Propofol was administered over a 155-minute period per dosing/treatment session, composed of two 70-minute low/high dosing regimens separated by a 15-minute transition dose. Propofol was infused from a 10 mg/ml preparation as follows:
Low dose: 3-min at 239 µg/kg/min; 6-min at 0 µg/kg/min; 61-min at 24 µg/kg/min
Transition dose: 15-min at 47 µg/kg/min
High dose: 3-min at 239 µg/kg/min; 6-min at 0 µg/kg/min; 61-min at 44 µg/kg/min Both products were for IV injection and were prepared as a sterile product ready for use per subject by the investigational pharmacy, according to the randomization schedule. To prevent treatment induced nausea, participants were administered ondansetron 4 mg IV approximately 15 minutes prior to dosing on each study day. To prepare the control product, placebo infusion bags containing Ringer's lactate were prepared, which matched the investigational product in appearance (batch numbers: 21H28E8M, 21F11E7C, and 21L10E3T). Thus, the matching placebo for Compound A consisted of the solution that was used as diluent for Compound A. Propofol 10 mg/mL for injection was provided as a sterile product ready for infusion (batch numbers 16QF1624 and 16QG1950). Compound A solution was colorless and its identity (prior to dilution and when mixed for injection) is similar to sterile normal saline solution or Ringer's lactate.

Performed after completion of all the treatments and procedures for the first 6 subjects of the study. The data (i.e., PD and safety reports) supporting interim analysis will be archived. Analysis will include blinded safety (AEs, BP, ECG) (unblinded if necessary) and PD parameters will include ventilatory measurements and $ETCO_2$. PD will be unblinded for treatment but not subject. Dosing of the last 6 subjects is not dependent on the interim analysis and will proceed in parallel. The primary PD endpoint was hypoxic sensitivity which was analyzed with a mixed model analysis of variance with the fixed factors treatment, condition and treatment by condition, and the random factors participant, participant by treatment and participant by condition (combination of propofol condition and ventilatory condition). The BIS was analyzed with a mixed model analysis of covariance with the fixed factors treatment, time, treatment by time, and the random factors participant, participant by treatment and participant by time and the pre-value as covariate. The general treatment effect and specific contrasts were reported with the estimated difference and the 95% confidence interval, the least square mean estimates, and the p-value.

The individual Compound A and propofol plasma concentrations were listed and plotted in panel plots for each Compound A treatment period using both a linear and log y-axis. The individual plasma Compound A and propofol concentrations were summarised by Compound A treatment period and time, and were also presented graphically as mean over time, with standard deviation as error bars. Summary statistics were provided including all plasma concentration samples irrespective of the sampling time. The individual PK parameters were summarised per treatment and propofol treatment interval and were presented graphically as boxplots.

Participant Disposition

A total of 45 participants were screened, and 14 participants were randomized. Per protocol, 12 participants were planned to be enrolled in the study. Two participants discontinued the study (one withdrew consent during first treatment visit, the other was excluded by the principal investigator after first treatment visit) and were replaced. Their data were used in the safety and PD analysis population, but no PK data were obtained for these participants. No important protocol deviations were identified that affected the study.

Pharmacodynamic Evaluation

Hypoxic Ventilatory Sensitivity

The hypoxic sensitivity (ventilation in L/min per % desaturation) was the primary PD outcome measure of the study. Hypoxic sensitivity is the marker of carotid body activity. In all participants, breathing increased during the hypoxic measurements. This was generally more profound during hypercapnia than during normocapnia.

Administration of Compound A resulted in a significant treatment effect on hypoxic sensitivity (p<0.001), as is shown in Table 1. This effect was irrespective of visit, as indicate dby "Period" not being significant, and was not impacted by the combination of two ventilatory conditions (i.e., normo- and hypercapnia) and three propofol dosing intervals, as indicated by "Treatment by Condition" not being significant. The separate contrasts of Compound A low and high dose versus placebo were calculated because the main treatment effect was significant. This showed that Compound A low dose trended toward a significant treatment effect, and that Compound A high dose was significant.

nounced in the Compound A high dose group.

Ventilatory Parameters

Figure 3:
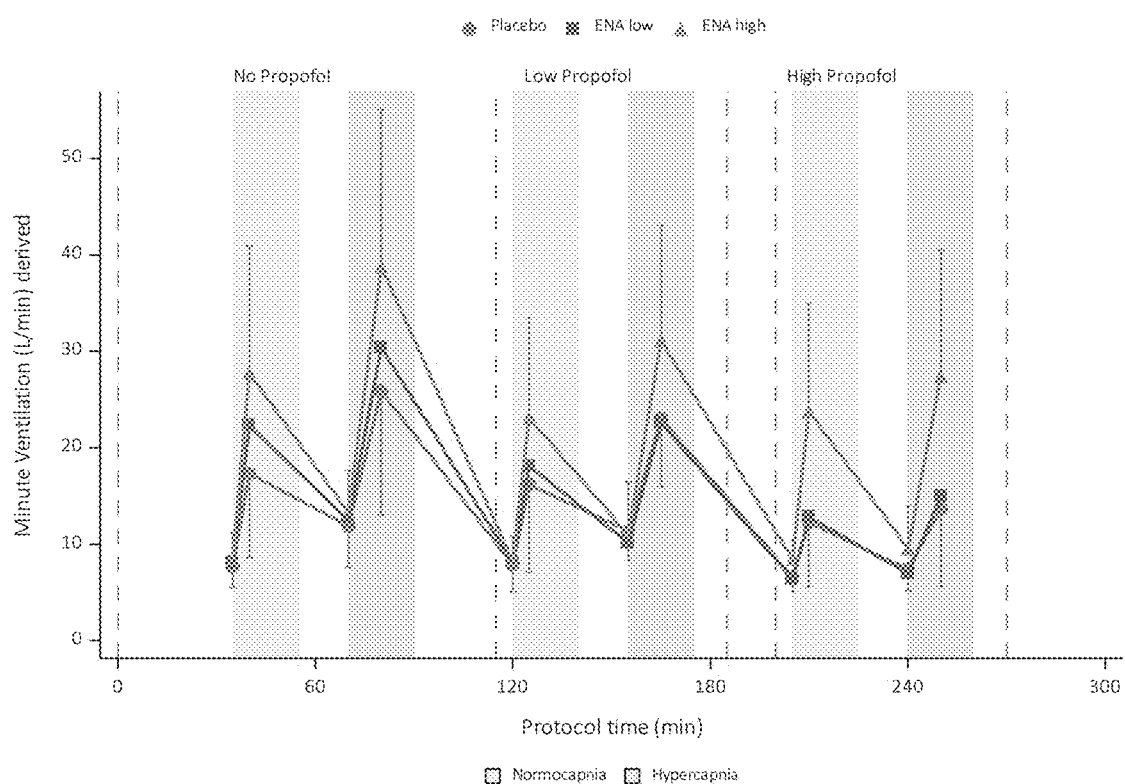
FIG. 3 is a graph representing the summary mean minute ventilation (L/min) of the Example.

During hypoxic measurements, mean minute ventilation increased compared to pre-hypoxic baseline in all treatments, as seen in FIG. 3, and a dose-dependent increase was observed for Compound A treatment. This increase became smaller after co-administration with propofol, which was especially evident in the placebo and Compound A low dose groups. During placebo treatment, minute ventilation increased from 7.7 L/min to 25.9 L/min during the first hypoxic measurement under hypercapnic conditions (i.e., without co-administration of propofol) and increased from 6.6 L/min to 13.7 min during the hypoxic/hypercapnic measurement during the propofol high dose administration. During treatment with Compound A low dose, minute ventilation increased from 8.1 L/min to 30.3 L/min during the first hypoxic measurement under hypercapnic conditions and increased from 6.3 L/min to 15.0 L/min during the hypoxic/hypercapnic measurement during the propofol high dose administration. During treatment with Compound A, however, minute ventilation increased from 8.5 L/min to 38.8 L/min during the first hypoxic measurement under hypercapnic conditions and increased from 8.4 L/min to 27.4 L/min during the hypoxic/hypercapnic measurement during the propofol high dose administration thereby maintaining a similar increase to pre-propofol levels after placebo treatment. Minute ventilation did not increase during treatment with Compound A when participants were not exposed to hypoxia.

Figure 4:
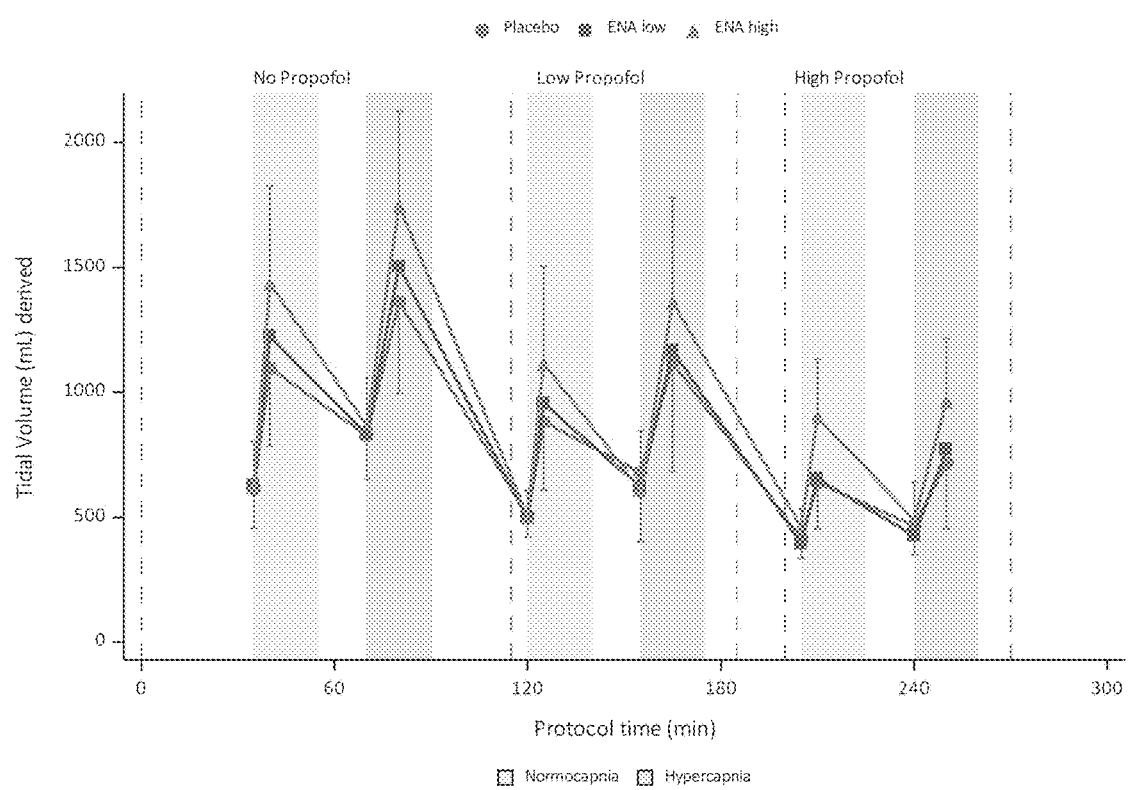
FIG. 4 is a graph representing the summary mean tidal volume (mL) of the Example.
Figure 5:
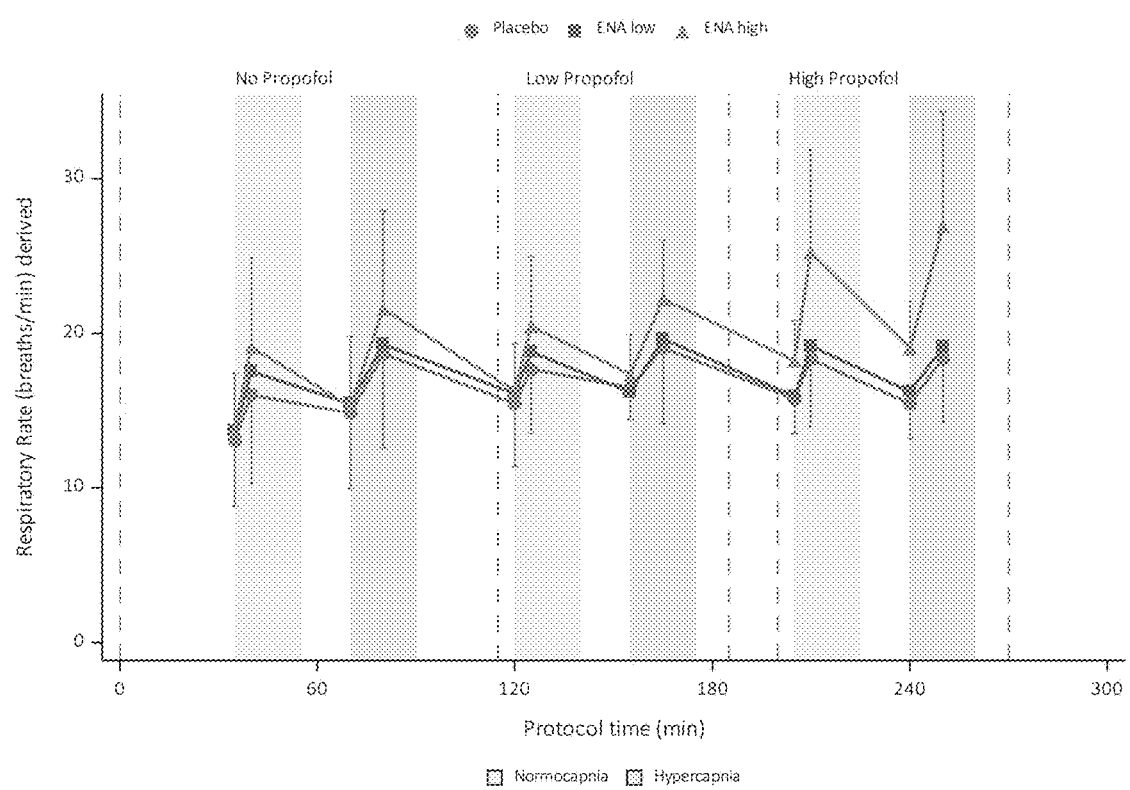
FIG. 5 is a graph representing the summary mean respiratory rate (breaths/min) of the Example.

Minute ventilation was a composite of tidal volume in mL per breath (FIG. 4) and respiratory rate in breaths per minute (FIG. 5). For these two parameters, the same trend was observed as for minute ventilation, thereby indicating that the increase in ventilation was a result both the increased volume of breath as well as the increased number of breaths drawn per minute. For respiratory rate, a difference between Compound A high dose compared to placebo and Compound A low dose could be observed during propofol infusion at pre-hypoxic timepoints.

TABLE 1

Analysis Results Hypoxic Sensitivity (L/min/%)

| Effect/Contrast | P-value | First LSM of contrast | Second LSM of contrast | Estimate of the difference | 95% CI Lower | 95% CI Upper |
|---|---|---|---|---|---|---|
| Treatment | <.0001 | — | — | — | — | — |
| Period | 0.8531 | — | — | — | — | — |
| Condition | <.0001 | — | — | — | — | — |
| Treatment by Condition | 0.4016 | — | — | — | — | — |
| Compound A low - Placebo | 0.0897 | 0.747 | 0.604 | 0.144 | −0.024 | 0.312 |
| Compound B high - Placebo | <.0001 | 1.179 | 0.604 | 0.575 | 0.407 | 0.744 |

Abbreviations:
CI = confidence interval;
ENA low = ENA-001 low dose;
ENA high = ENA-001 high dose;
LSM = least square means.

Figure 2:
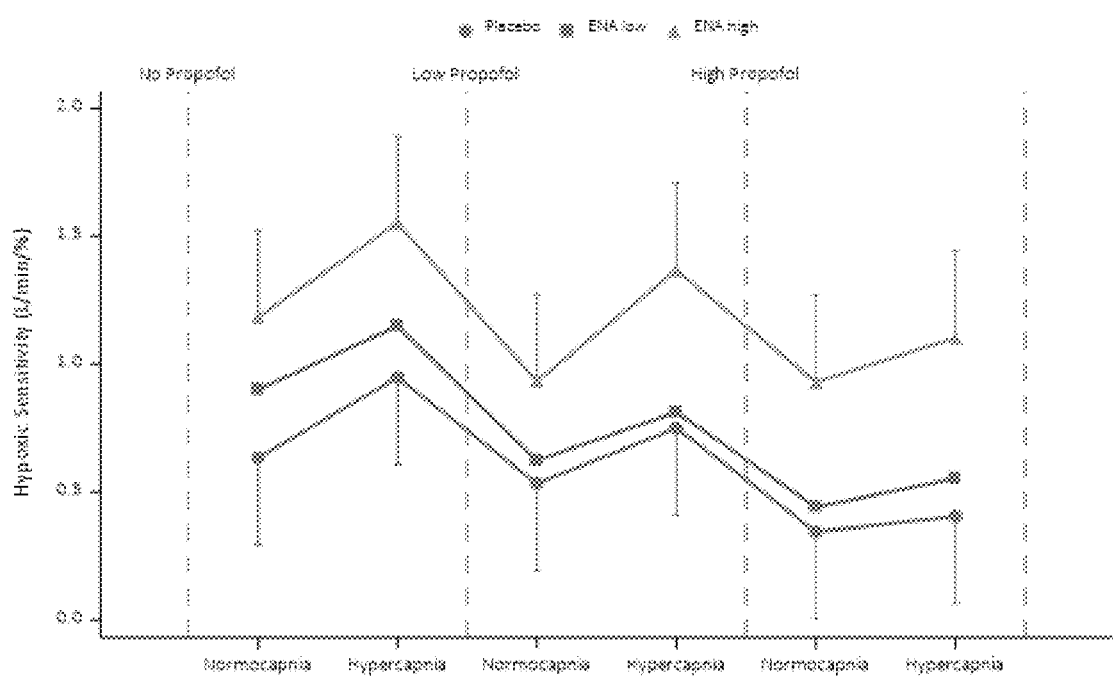
FIG. 2 is a graph representing the estimated means hypoxic sensitivity (L/min/%) of the Example.
Figure 6:
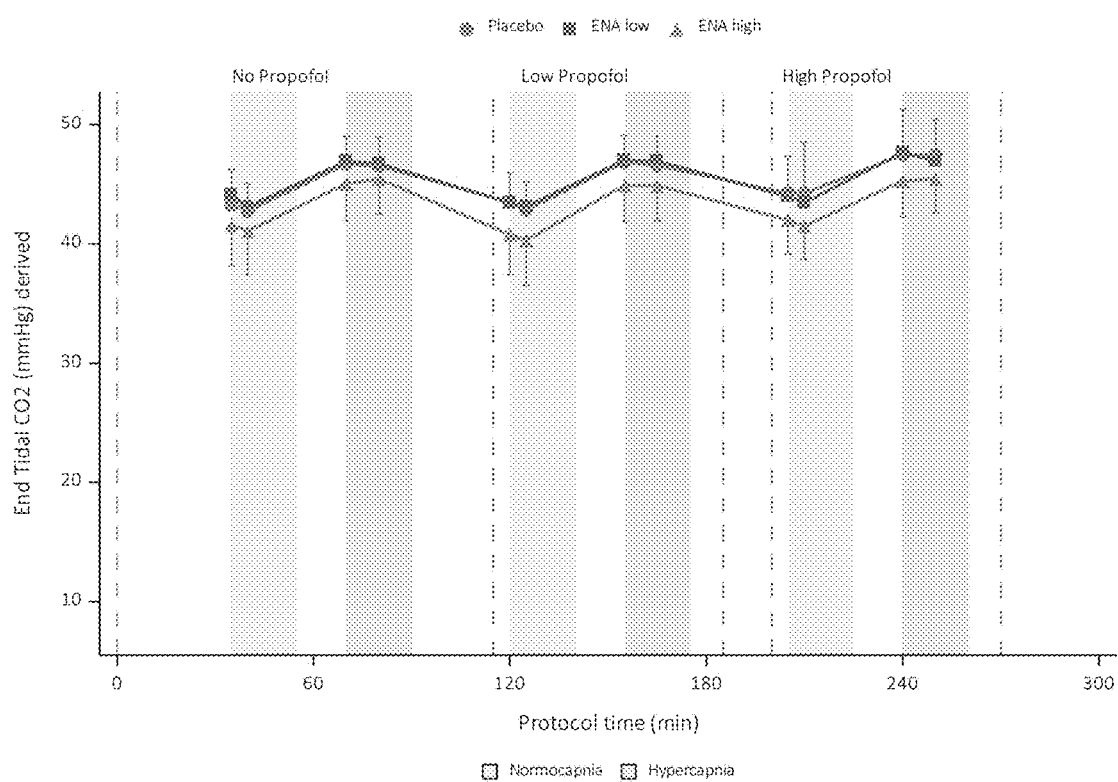
FIG. 6 is a graph representing the summary mean end tidal CO2 (mmHg)

As is evident by FIG. 2, propofol decreased hypoxic sensitivity during placebo infusion and diminished in particular the additional effect of hypercapnia during the propofol high dose. Concomitant administration of Compound A high dose, however, appeared to cause the hypoxic sensitivity to remain similar to pre-propofol values. Also, the (physiolocial) increase in minute ventilation induced by hypercapnia during high dose propofol was more pro- The $ETCO_2$ (FIG. 6) was increased after the first hypoxic measurement of each propofol dosing interval in order to perform another hypoxic measurement at hypercapnia. Values recorded for Compound A low dose were comparable to placebo treatment. However, at both pre-hypoxic timepoints as well as during hypoxia and hypercapnia, the values recorded for Compound A high dose were lower compared to placebo. Although no statistical analysis was defined for ETCO$_2$ in the statistical analysis plan, the difference between treatments was evidence from the summary graph in FIG. 6.

Figure 7:
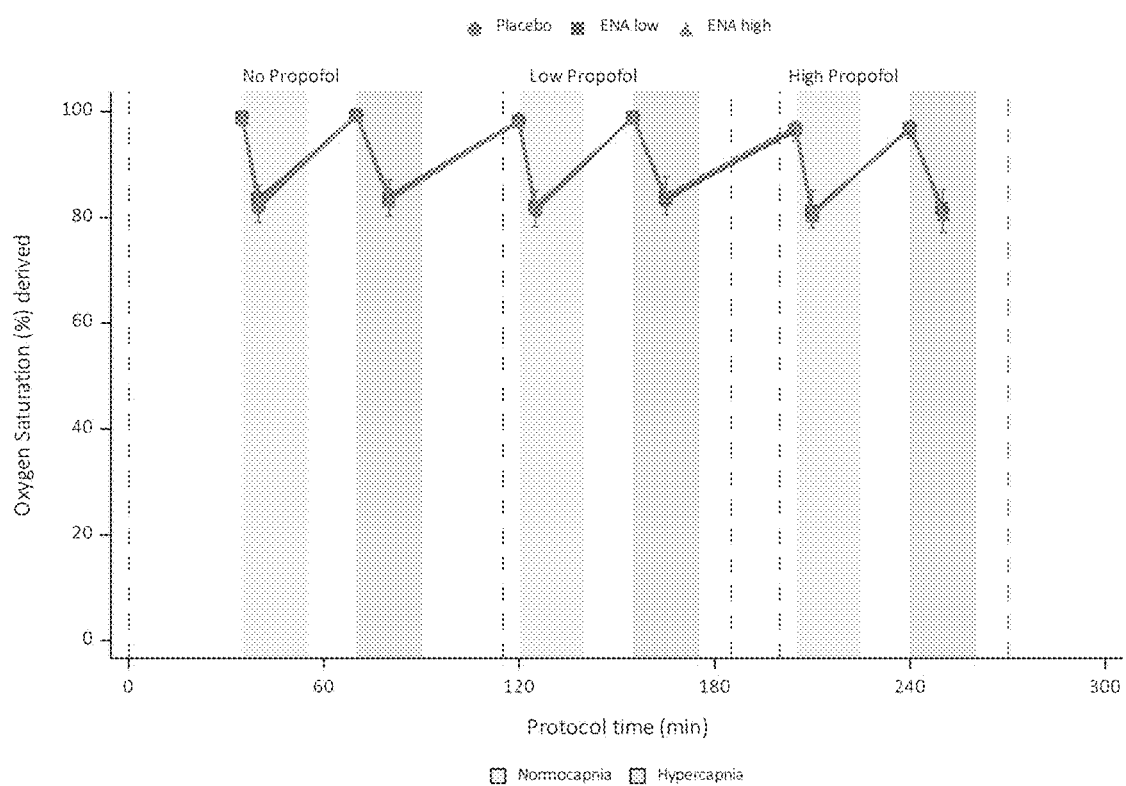
FIG. 7 is a graph representing the summary mean oxygen saturation (%)

The oxygen saturation SpO$_2$ was also measured and shown in FIG. 7. The SpO$_2$ remained above 96.4% at all pre-hypoxic baseline timepoints for all three treatments. During hypoxic measurements, SpO$_2$ ranged 80.4-84.3%, 81.2-83.7%, 80.4-84.2% for placebo, Compound A low and high dose, respectively. Given that the SpO$_2$ was steered during measurements by the investigator-controlled inhaled gas mix, this did not regard an independent variable but rather a confirmation that the measurements were performed per protocol.

Summary of Pharmacodynamic Findings

From the above study, it was found that (1) Compound A resulted in a significant treatment effect (p<0.0001) on the primary PD outcome measure of the study, hypoxic sensitivity, versus placebo; (2) Mean minute ventilation increased during hypoxic measurements in all treatments, with a dose-dependent increase observed for Compound A; (3) An increase during hypoxic measurements was observed for mean tidal volume and respiratory rate in all treatments, indicating that the increase in minute ventilation was a result of the increase in both these parameters; (4) Mean ETCO$_2$ values recorded for Compound A high dose were evidently lower at all timepoints compared to Compound A low dose and placebo (both at pre-hypoxic timepoints as well as during hypoxia and hypercapnia); (5) Controlled SpO$_2$ values were within targeted ranges per protocol; (6) No difference between treatments was observed on the mean BIS value; (7) No clinically meaningful difference on cardiovascular response was observed after treatment with Compound A versus placebo; and (8) No clinically meaningful difference on arterial blood gases was observed after treatment with Compound A versus placebo.

Pharmacokinetics Evaluation

Figure 8:
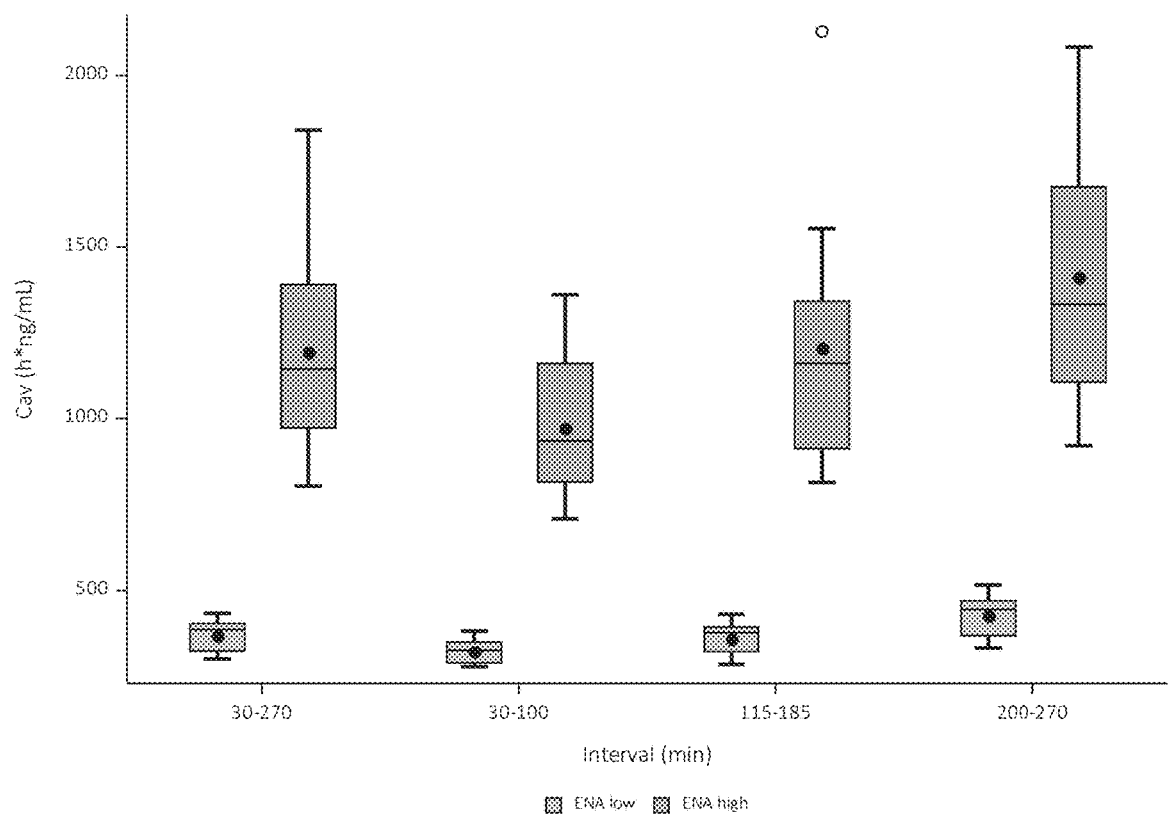
FIG. 8 is a graph representing the average plasma concentrations of Compound A of the Example by Propofol Dosing Interval.

Pharmacokinetic samples were measured up to 24 hours after the start of the IV infusion. Concentrations reached a maximum level of 857.000 and 1162.833 ng/mL on average following the 10 minutes and 20 minutes IV infusion loading dose of Compound A low and high dose, respectively. Therefore, a fast decrease in concentration was observed, followed by a slow increase. Based on visual inspection of the PK profile and the average concentrations per propofol dosing interval (FIG. 8), steady-state concentrations were not reached within the 260 and 250 minute infusions thereafter.

Figure 9:
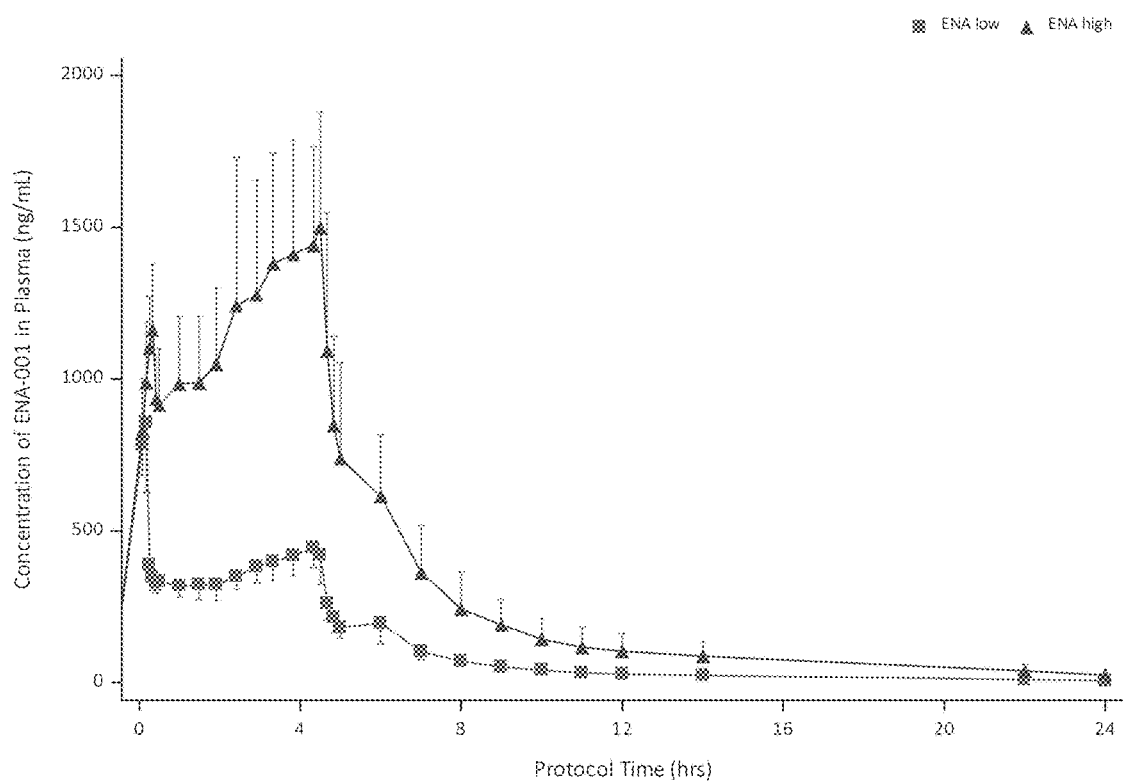
FIG. 9 is a graph representing the mean plasma Compound A concentration-time profiles following administration of Compound A of the Example (Normal Scale)
Figure 10:
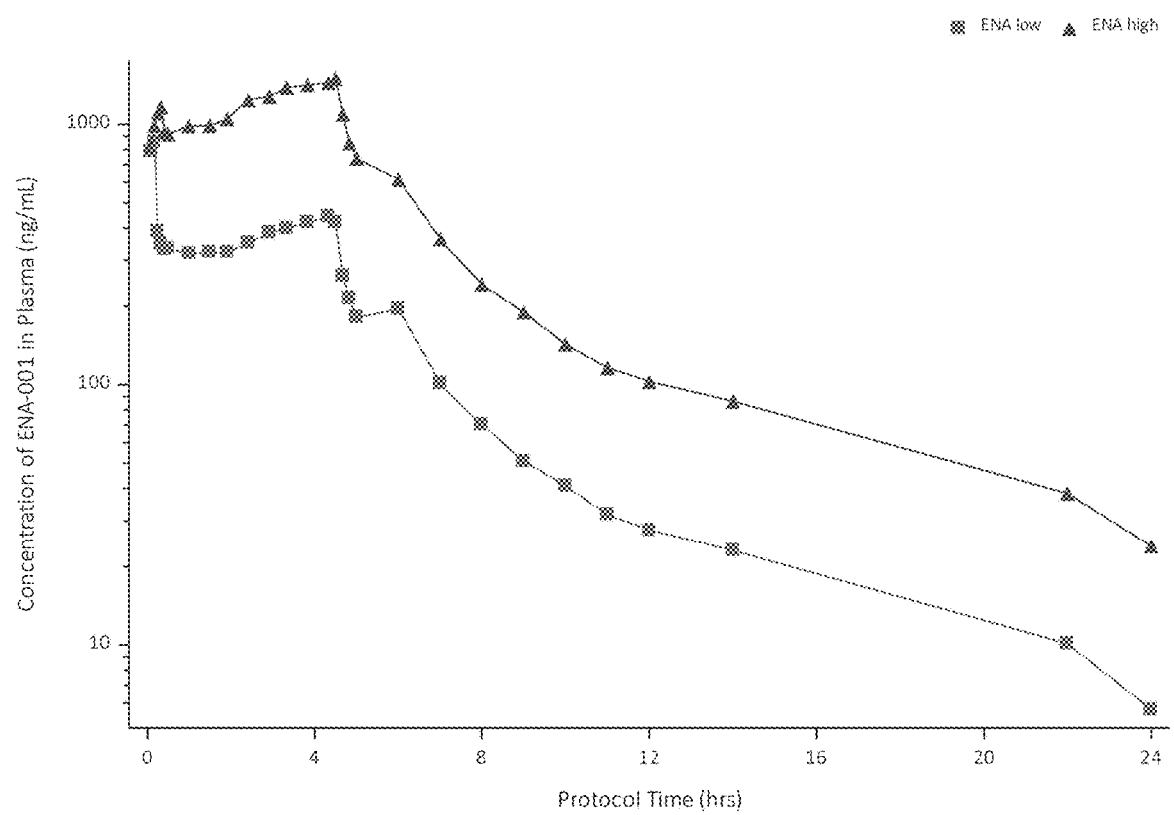
FIG. 10 is a graph representing the mean plasma Compound A concentration-time profiles following administration of Compound A of the Example with a Logarithmic Y-axis

The Compound A plasma concentrations decreased rapidly after continuous infusion was stopped. From 4 hour 30 minutes onwards, the Compound A plasma concentrations followed a bi-exponential decline (FIGS. 9 and 10). At 5 hours, the blood sampling from the arterial line was stopped and venous samples were collected thereafter. Values were above the LLOQ at 24 hours post-dose in all participants for both Compound A dose levels.

Pharmacokinetic parameters are presented in Table 2. Mean peak concentrations occurred at the end of infusion, at a $t_{max}$ of 4.260 hours for Compound A low dose and at 3.965 hours for Compound A high dose. A mean ($\pm$SD) $C_{max}$ of 467.9$\pm$68.20 ng/mL for Compound A low dose and 1557.5$\pm$437.02 ng/mL for Compound A high dose was observed, with a mean ($\pm$SD) AUC$_{inf}$ of 2674.9$\pm$330.47 and 8711.4$\pm$2422.64 ng*h/mL, respectively. The highest individual $C_{max}$ reached with the Compound A high dose was 2600 ng/mL, the highest individual AUC$_{inf}$ reached with the Compound A high dose was 13763 ng*h/mL. The average Compound A concentrations increased with increasing propofol dosing intervals (i.e., no propofol 30-100 min, low propofol 115-185 min, and high propofol 200-270 min): the average concentrations for Compound A low dose were 323.41, 359.75, and 427.54 ng/mL, respectively, and for Compound A high dose these were 971.79, 1206.27, and 1412.28 ng/mL, respectively. Geometric mean $C_{av30-270\ min}$ (average arterial plasma ENA-001 concentration during 30-270 min) for Compound A low and high dose were 366.40 and 1161.69 ng/mL, respectively. The increase was not considered related to the propofol dose but rather to the fact that steady state had not been reached.

The ranges of the mean apparent terminal $t_{1/2}$ were similar in the Compound A low and high dose groups (3.00-6.99 and 3.39-8.40 hours, respectively). Low variability, as indicated by the CV of <25%, was observed in all PK parameters for the Compound A low dose except for $t_{min}$, which had a CV of 39.5%. Low to moderate variability (CV ranging between 21.1-36.2%) was observed in all parameters for the Compound A high dose except for $t_{min}$, which had a CV of 82.1%. Average $t_{min}$ was 1.201 hours for the Compound A low dose and 1.133 hours for the Compound A high dose. The sample scheduled at the 3 h20 m timepoint was drawn later than planned in participant 6 during Compound A high dose, after the infusion was temporarily interrupted for several minutes due to a toilet break. This caused the Compound A plasma concentration to be clearly lower than expected for that timepoint.

Dose proportionality of PK over the investigated dosing range was apparent, based on the dose normalised values of AUC$_{inf}$ and $C_{av}$. No apparent interaction between Compound A was observed, based on the PK parameters related to Compound A infusion.

| Treatment | Parameter | Unit | N | Mean | Geometric Mean | SD | CV (%) | Geometric CV (%) | Median | Min | Max |
| --- | --- | --- | --- | --- | --- | --- | --- | --- | --- | --- | --- |
| ENA low | AUC$_{inf}$ | h*ng/mL | 12 | 2674.9 | 2656.1 | 330.47 | 12.4 | 12.5 | 2654 | 2155 | 3148 |
|  | AUC$_{last}$ | h*ng/mL | 12 | 2628.3 | 2610.3 | 320.52 | 12.2 | 12.3 | 2631 | 2151 | 3059 |
|  | CL | L/h | 12 | 55.75 | 55.08 | 9.298 | 16.7 | 16.1 | 53.1 | 41.9 | 75.5 |
|  | $t_{1/2}$ | h | 12 | 5.104 | 4.988 | 1.1040 | 21.6 | 23.2 | 5.05 | 3.00 | 6.99 |
|  | $C_{max}$ | ng/mL | 12 | 467.9 | 463.3 | 68.20 | 14.6 | 14.8 | 477 | 375 | 563 |
|  | Cm$_{in}$ | ng/mL | 12 | 302.3 | 299.6 | 42.54 | 14.1 | 14.0 | 296 | 251 | 379 |
|  | $t_{max}$ | h | 12 | 4.260 | 4.246 | 0.3438 | 8.1 | 8.8 | 4.33 | 3.33 | 4.50 |
| ENA high | AUC$_{inf}$ | h*ng/mL | 12 | 8711.4 | 8442.2 | 2422.64 | 27.8 | 25.8 | 7796 | 6235 | 13763 |
|  | AUC$_{last}$ | h*ng/mL | 12 | 8504.6 | 8241.9 | 2355.57 | 27.7 | 25.9 | 7545 | 6169 | 13169 |
|  | CL | L/h | 12 | 45.34 | 44.07 | 10.809 | 23.8 | 26.1 | 46.3 | 23.8 | 67.8 |
|  | $t_{1/2}$ | h | 12 | 5.643 | 5.492 | 1.3657 | 24.2 | 24.9 | 5.63 | 3.39 | 8.40 |
|  | $C_{max}$ | ng/mL | 12 | 1557.5 | 1508.2 | 437.02 | 28.1 | 26.3 | 1520 | 1090 | 2600 |

-continued

| Treatment | Parameter | Unit | N | Mean | Geometric Mean | SD | CV (%) | Geometric CV (%) | Median | Min | Max |
|---|---|---|---|---|---|---|---|---|---|---|---|
| | $C_{min}$ | ng/mL | 12 | 886.6 | 867.4 | 194.25 | 21.9 | 22.1 | 859 | 601 | 1230 |
| | $t_{max}$ | h | 12 | 3.965 | 3.840 | 0.9008 | 22.7 | 29.1 | 4.36 | 1.92 | 4.50 |

Abbreviations:
$AUC_{inf}$ = area under the concentration-time curve from time 0 to infinity;
$AUC_{last}$ = area under the concentration-time curve from time 0 to last measured concentration;
CL = clearance;
$C_{max}$ = maximum concentration;
$C_{min}$ = minimum concentration;
CV = coefficient of variation;
ENA low = ENA-001 low dose;
ENA high = ENA-001 high dose;
SD = standard deviation;
$t_{max}$ = time to maximum concentration;
$t_{1/2}$ = half-life.

Summary of Pharmacokinetic Results of Compound A

From the above study, it was found that (1) the plasma concentrations of Compound A followed a bi-exponential decline with an apparent terminal $t_{1/2}$ for the low and high Compound A dose (ranging between 3.00-6.99 and 3.39-8.40 hours for the low and high dose, respectively); (2) Plasma concentrations increased over time and peaked at approximately 3.965 hours at mean (±SD) peak concentrations of 1557.5±437.02 ng/mL at the high dose level (2 mg/kg/h for 20 minutes followed by 1.1 mg/kg/h for 250 minutes); (3) A mean (±SD) $AUC_{inf}$ of 8711.4±2422.64 ng*h/mL was reached for the highest dose level studied; (4) Geometric mean $C_{av30\text{-}270\ min}$ (average arterial plasma Compound A concentration during 30-270 min) for Compound A low and high dose were 366.40 and 1161.69 ng/mL, respectively; (5) The average Compound A concentrations increased with increasing propofol dosing interval: for Compound A low dose these were 323.41, 359.75, and 427.54 ng/mL, respectively, and for ENA-001 high dose these were 971.79, 1206.27, and 1412.28 ng/mL, respectively; (6) Dose proportionality of PK was apparent over the investigated dosing range and low-to-moderate levels of inter-individual variability in the $C_{max}$, distribution, and elimination phase were observed; and (7) No apparent effect of propofol on Compound A concentrations was observed.

Pharmacokinetic Results Propofol

The pharmacokinetic results of propofol were also studied and found to be: (1) Plasma concentrations increased over time and peaked at mean (±SD) concentrations of 1880.8±265.45, 2534.2±1192.34, and 2620.0±1093.86 ng/mL during infusion with placebo and Compound A low and high dose, respectively; (2) Geometric mean $C_{av115\text{-}185\ min}$ and $C_{av200\text{-}270\ min}$ (average arterial plasma concentration during 115-185 min propofol low dose interval and 200-270 min propofol high dose interval, respectively) for propofol ranged between 452.62-559.80 and 1525.12-1862.45 ng/mL, respectively; (3) Mean $AUC_{last}$ of 4599.1±547.80, 5745.9±1181.39, and 6151.6±1166.70 ng*h/mL were reached during infusion with placebo and Compound A low and high dose, respectively; (4) A greater than dose proportional increase in plasma concentration was apparent over the investigated dosing range and low levels of inter-individual variability in the distribution and elimination phase were observed, but high levels of inter-individual variability in $C_{max}$ were observed during co-administration with Compound A; and (5) Propofol plasma concentrations tended to be higher during infusion with Compound A compared to those during placebo infusion, although no apparent effect of the dose level was observed Exposure:

A total of 12 participants were exposed to two dose levels of Compound A administered as continuous infusion for 270 minutes, as described under methodology. These 12 participants were also exposed placebo treatment. Two discontinued participants were exposed only to the high dose of Compound A: one participant discontinued treatment after 97 minutes and the other participant completed the first treatment visit but was excluded thereafter due to his reaction to propofol.

From this, it was concluded that Compound A was safe and well tolerated in healthy participants at the two dose levels administered in this study. Treatment with Compound A increased hypoxic sensitivity compared to placebo, both with and without co-administration of clinically relevant plasma concentrations of propofol. Also, administration of Compound A did not impact the level of the propofol-induced sedation, as measured by the BIS.

From this study, it was found that Compound A resulted in a significant treatment effect (p<0.0001) on the primary PD outcome measure of the study, hypoxic sensitivity, versus placebo. Additionally, mean minute ventilation increased during hypoxic measurements in all treatments, with a dose dependent increase observed for Compound A. An increase during hypoxic measurements was observed for mean tidal volume and respiratory rate in all treatments, indicating that the increase in minute ventilation was a result of the increase in both these parameters. Also, mean ETCO2 values recorded for Compound A high dose were evidently lower at all timepoints compared to Compound A low dose and placebo (both at pre-hypoxic timepoints as well as during hypoxia and hypercapnia). It was also found that controlled SpO2 values were within targeted ranges per protocol. No difference between treatments was observed on the mean BIS value. No clinically meaningful difference on cardiovascular response was observed after treatment with Compound A versus placebo. No clinically meaningful difference on arterial blood gases was observed after treatment with Compound A versus placebo.

Evaluation of Response to Study Treatment

The main objectives of this study were to determine the safety, tolerability, and ventilatory response of Compound A infusions in healthy participants after low and high doses of Compound A under hypoxic and hypercapnic conditions in conjunction with low and high doses of propofol.

Presented safety data indicated that Compound A has favourable safety and tolerability profiles in healthy participants at the two doses administered in this study. No treatment-related SAEs occurred in this study. Apart from mild infusion site pain and related events, which were expected based on previous studies with Compound A, no trend in AEs was recorded. Moreover, the only participant who developed phlebitis received placebo. Additionally, given that nausea was associated with Compound A administration in previous studies, all participants received IV ondansetron prior to the start of each treatment period. As a result, only a single occurrence of mild nausea probably related to Compound A treatment was recorded, in a participant who received Compound A high dose. No clinically meaningful differences between treatments were identified in any other safety parameter.

The primary PD endpoint of the study was hypoxic sensitivity, defined by the increase in minute ventilation as a function of the decrease in $SpO_2$ ($\Delta$Ventilation/$\Delta$Saturation=hypoxic sensitivity in L/min per % desaturation). Summary graphs showed that the decrease in blood oxygen levels as a result of hypoxia and the increase in $ETCO_2$ during the hypercapnic measurements were as targeted per protocol. As expected, a decrease of hypoxic sensitivity was observed as a result of propofol infusion. Concomitant administration of 1.1 mg/kg/h Compound A (high dose) caused a significant increase in the hypoxic sensitivity and caused it to remain similar to pre-propofol values. When analysing the Compound A low and high doses separately, the low dose trended toward a significant effect but only the high dose yielded a statistically significant result versus placebo. This could be expected based on data from previous studies in which the Compound A low dose (0.4 mg/kg/h) showed no/minimal stimulatory effects on minute ventilation (McLeod et al., 2014) whereas the Compound A high dose (1.1 mg/kg/h) produced clear ventilatory stimulation in healthy participants and significantly attenuated alfentanil-induced ventilatory suppression (Roozekrans et al., 2014).

Importantly, the finding that minute ventilation only increased during hypoxic measurements indicated that the administered doses of Compound A did not lead to hyperventilation during breathing of room air. The administration of Compound A only bolstered the ventilatory reaction to oxygen desaturation.

In addition, lower values of $ETCO_2$ prior to each hypoxic measurement were consistently observed for Compound A high dose compared to placebo and Compound A low dose. Although the difference of approximately 3 mmHg may not be clinically meaningful, these data suggested that a shift across the metabolic hyperbola due to respiratory stimulation took place which is reflected by the decrease in $ETCO_2$ without yet increasing minute ventilation.

Despite the clear ventilatory response, administration of Compound A did not lead to a significant difference in arousal compared to placebo, as measured by the BIS, after administration of clinically relevant doses of propofol, which were comparable to sedation anaesthesia. In other words, the level of sedation of propofol was as expected at targeted plasma concentrations, and no apparent difference was observed between treatments. Furthermore, no clinically meaningful difference in the cardiovascular response was observed between treatments. These findings strengthen the case for use of Compound A in clinical practice, where the goal is a ventilatory response without influencing the effect of other administered drugs.

The infusion regimens in the current study were designed to maintain stable Compound A and propofol (low and high dose) concentrations during the respective dosing intervals. The PK of Compound A showed dose proportionality over the investigated dosing range, and exposure levels were in the targeted range, based on PK modelling that was performed in preparation of this study. Low levels of inter-individual variability in the $C_{max}$, distribution, and elimination phase were observed. However, Compound A did not reach steady state and concentrations increased during continuous infusion until infusion was stopped. Plasma concentration differences were not reflected in safety parameters and the ventilatory response of Compound A was evident throughout the treatment period. No apparent effect of propofol on Compound A concentrations were observed.

The relationship between Compound A plasma concentrations and the PD response is further described in a separate PK-PD modelling report.

The propofol dosing regimen was designed to simulate infusion with a target-controlled infusion pump, targeting plasma concentration of 600 and 1200 ng/mL during the propofol low and high dose, respectively. Plasma concentrations during the low dose infusion were similar to the targeted concentration, but the high dose resulted in plasma concentrations exceeding those targeted. Dose proportionality of propofol PK over the investigated dosing range was not apparent, with relatively higher plasma concentrations recorded during the high dose infusion. It must be noted that despite these higher propofol plasma concentrations, the effect of Compound A on ventilation was significant.

From this study, it can be concluded that Compound A is safe and well tolerated in healthy participants at the two dose levels administered in the study. Treatment with Compound A increased hypoxic sensitivity compared to placebo, both with and without co-administration of clinically relevant plasma concentrations of propofol. Administration of Compound A did not impact the level of the propofol-induced sedation, as measured by the BIS.

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. Reference throughout this specification to "an embodiment", "certain embodiments", or "one embodiment" means that a particular feature, structure, or characteristic described in connection with the embodiment is included in at least one embodiment.

Thus, the appearances of the phrase "an embodiment", "certain embodiments", or "one embodiment" in various places throughout this specification are not necessarily all referring to the same embodiment.

The present invention has been described with reference to specific exemplary embodiments thereof. The specification and drawings are, accordingly, to be regarded in an illustrative rather than a restrictive sense. Various modifications of the invention in addition to those shown and described herein will become apparent to those skilled in the art and are intended to fall within the scope of the appended claims.

What is claimed is:

1. A method of treating respiratory depression caused by a non-opioid agent comprising administering, to a patient in need thereof, an effective amount of the compound,

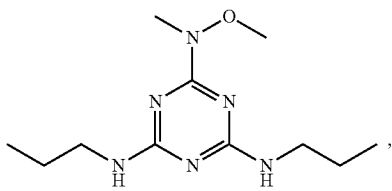 [SMILES: CCCNc1nc(NCCC)nc(N(C)OC)n1 ; ","]

or a pharmaceutically effective salt thereof, wherein the non-opioid agent is propofol, or a pharmaceutically acceptable salt thereof.

2. The method of claim 1, wherein the patient exhibits a restored ventilatory sufficiency.

3. The method of claim 2, wherein the patient exhibits restored ventilator sufficiency under normal sedation, under low sedation or under high sedation.

4. The method of claim 2, wherein the patient exhibits restored ventilator sufficiency under overdose.

5. The method of claim 1, wherein the patient shows increased ventilatory responsiveness.

6. The method of claim 5, wherein the patient shows increased ventilatory responsiveness to hypoxemic events.

7. The method of claim 5, wherein the patient shows increased ventilatory responsiveness to hypercapnic events.

8. The method of claim 1, wherein the administration route is selected from oral, intravenous, nasal, inhalational, topical, buccal, rectal, pleural, peritoneal, vaginal, intramuscular, subcutaneous, transdermal, epidural, intratrachael, otic, intraocular, or intrathecal route.

* * * * *